United States Patent
Nandabalan et al.

(10) Patent No.: US 11,613,785 B2
(45) Date of Patent: Mar. 28, 2023

(54) PREDICTIVE AND DIAGNOSTIC METHODS FOR PROSTATE CANCER

(71) Applicant: OnkosXcel Therapeutics, LLC, New Haven, CT (US)

(72) Inventors: Krishnan Nandabalan, New Haven, CT (US); Luca Rastelli, New Haven, CT (US)

(73) Assignee: OnkosXcel Therapeutics, LLC, New Haven, CT (US)

( * ) Notice: Subject to any disclaimer, the term of this patent is extended or adjusted under 35 U.S.C. 154(b) by 541 days.

(21) Appl. No.: 16/476,420

(22) PCT Filed: Jan. 9, 2018

(86) PCT No.: PCT/US2018/012876
§ 371 (c)(1),
(2) Date: Jul. 8, 2019

(87) PCT Pub. No.: WO2018/129497
PCT Pub. Date: Jul. 12, 2018

(65) Prior Publication Data
US 2021/0355541 A1  Nov. 18, 2021

Related U.S. Application Data

(60) Provisional application No. 62/561,218, filed on Sep. 21, 2017, provisional application No. 62/473,507, filed on Mar. 20, 2017, provisional application No. 62/443,831, filed on Jan. 9, 2017.

(51) Int. Cl.
*C12Q 1/6886* (2018.01)
*G16B 25/10* (2019.01)

(52) U.S. Cl.
CPC .......... *C12Q 1/6886* (2013.01); *G16B 25/10* (2019.02); *C12Q 2600/118* (2013.01); *C12Q 2600/158* (2013.01)

(58) Field of Classification Search
CPC .................................................. C12Q 1/6886
USPC ..................................................... 424/133.1
See application file for complete search history.

(56) References Cited

FOREIGN PATENT DOCUMENTS

WO  WO 2017/011831 A1  1/2017
WO  WO 2018/129497 A1  7/2018

OTHER PUBLICATIONS

Massari et al (Targ Oncol, 2016, 11: 345-351).*
Graff et al (Annals of Oncology, 2016, 27(S6)(vi243-vi265): Abstract 7190).*
Da Silva et al (Nature Immunology, 2015, 16(8): 850-858).*
Wilson et al (The Journal of Urology, 2005, 174: 1124-1128).*
Cunningham (Expert Opin on Invest Drugs, 2007, 9: 1459-1465).*
Extended European Search Report for European Application No. 18736583.8 dated Dec. 11, 2020.
Feig et al., "Targeting CXCL12 from F AP-expressing carcinoma-associated fibroblasts synergizes with anti-PD-LI immunotherapy in pancreatic cancer," PNAS, Dec. 2013, 110(50): 20212-20217.
Fearon, D., "The Carcinoma-Associated Fibroblast Expressing Fibroblast Activation Protein and Escape from Immune Surveillance," Cancer Immunol Res, 2014; 2(3):187-193.
Goltz et al., "CXCL12 promoter methylation and PD-L1 expression as prognostic biomarkers in prostate cancer patients," Oncotarget, 2016, vol. 7, No. 33, pp. 53309-55230.
International Search Report and Written Opinion of the International Searching Authority for International Application No. PCT/US2018/012876 dated May 11, 2018, 14 pages.
Okondo et al., "DPP8 and DPP9 inhibition induces pro-caspase-1-dependent monocyte and macrophage pyroptosis," Nature Chemical Biology, Jan. 2017, vol. 13, pp. 46-53.
Ylitalo et al., "Subgroups of Castration-resistant Prostate Cancer Bone Metastases Defined Through an Inverse Relationship Between Androgen Receptor Activity and Immune Response," European Urology, 2017, 71:776-787.

* cited by examiner

*Primary Examiner* — Sean E Aeder
(74) *Attorney, Agent, or Firm* — Cooley LLP

(57) ABSTRACT

The present invention generally relates to a method of diagnosing, prognosing and treating prostate cancer patients. Particularly, the present invention relates to a method of selecting patients with castration resistant prostate cancer (CrPC) for combination therapy comprising a selective dipeptidyl peptidase inhibitor and a PD-1 axis antagonist. The present invention provides a computational approach to identifying potential patients for CrPC. The present invention also relates to a method of treating castration resistant prostate cancer (CrPC) patients with said combination therapy.

21 Claims, 1 Drawing Sheet
Specification includes a Sequence Listing.

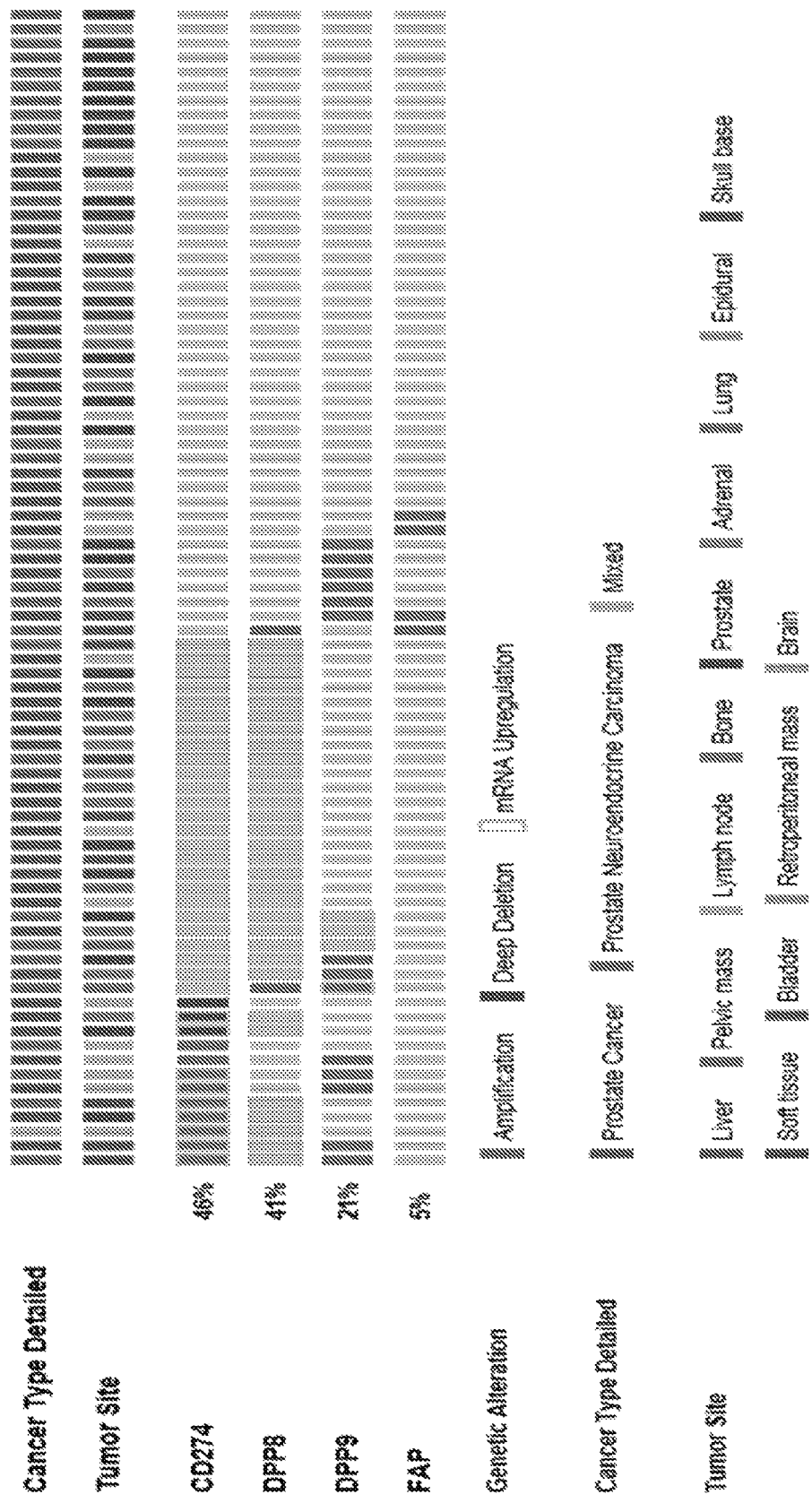

PREDICTIVE AND DIAGNOSTIC METHODS FOR PROSTATE CANCER

FIELD OF THE INVENTION

The present invention generally relates to a method of diagnosing, prognosing and treating prostate cancer patients. Particularly, the present invention relates to a method of selecting patients with castration resistant prostate cancer (CrPC) for combination therapy comprising a selective dipeptidyl peptidase inhibitor and a PD-1 axis antagonist. The present invention provides a computational approach to identifying potential patient segment for the said combination therapy. The present invention also relates to a method of treating castration resistant prostate cancer (CrPC) patients with said combination therapy.

CROSS REFERENCE TO RELATED APPLICATION

This application is the U.S. National Stage of international Patent Application No. PCT/US2018/012876, filed Jan. 9, 2018, which claims the benefit of priority to U.S. Provisional Application No. 62/443,831 filed on Jan. 9, 2017, U.S. Provisional Application 62/473,507 filed on Mar. 20, 2017, and U.S. Provisional Application No. 62/561,218 filed on Sep. 21, 2017 the disclosures of which are herein incorporated by reference in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BXTI_017_03_US_SeqList_ST25.txt, date recorded: Jul. 8, 2019, file size: kilobytes).

BACKGROUND OF THE INVENTION

Today our healthcare system is riddled with inefficiency and wasteful spending, one example of this is that the efficacy rate of many oncology therapeutics working only about 25% of the time. Many of those cancer patients are experiencing unwanted side effects for costly therapies that may not be working. This imbalance between high treatment costs and low therapeutic efficacy is often a result of treating a specific diagnosis one way across a diverse patient population. But with the advent of gene profiling tools, genomic testing, and advanced diagnostics, this is beginning to change.

The current practice of drug discovery in cancer is based upon the assumption that the same molecular and cellular processes that build a cancer, when tackled, will kill the cancer. This has indeed been shown for several selected, single oncogene-dependent cancers. This approach invariably relies on the analysis of gene expression studies that have typically focused on identification of differentially expressed genes or pathways. However, this approach is limited, because genes do not function in isolation, they work in concert.

So, now a days a different kind of approach, comprising the use of the analysis of genomic, proteomic, exomic or transcriptomic data of patients, is being utilized to study the amplification arid/or expression level of several targets and their gene patterns to identify the patient segment and treatment options.

For the past 30 years, castration resistant prostate cancer (CrPC) mortality rate has remained high and unchanged, despite considerable efforts directed toward this disease. Since, CrPC frequently exhibits very high tumor heterogeneity, genome instability and altered gene expression, which makes the proper subtype identification and signature discovery of CrPC essential tasks for facilitating the development of more effective therapeutic regimens. There are only a few medications registered for the treatment of CrPC now: Docetaxel (Taxotere®) and Cabazitaxel (Jevtana®) both of which are cytostatics, plus Abiraterone (Zytiga®), Enzalutamide (Xtandi®) and Radium-223 (Xofigo®). Abiraterone and Enzalutamide are hormonally active (impair/block), whilst Radium-223 binds to the area of the skeleton where subsidiary tumors (metastases) are located and releases a local radioactive effect there. These five drugs have been shown to impair the tumor disease in most patients, and extend survival by around 2.5-5 months. All have side effects to some degree, and individual patient status will determine the therapy that can be used. Every single one of these medications has a relatively short efficacy time, as the disease becomes resistant to the drug after a short period, which means it must be replaced by another. There are no curative medications currently in sight.

Hence, due to the high incidence and severe complexity of castration resistant prostate cancer (CrPC), there is a continuing need in the art for diagnostic and/or predictive markers of response and treatment option for said cancer. The present inventors investigated the use of gene amplification and/or expression network analyses and identified that the selective dipeptidyl peptidases (DPP-8/DPP-9/FAP) and PDL-1 genes can work as a potential predictive markers for the castration resistant prostate cancer (CrPC) to improve its diagnosis/prognosis process and thus provides a unique combination of selective dipeptidyl peptidases inhibitor, more specifically DPP-8/DPP-9/FAP inhibitor along with a programmed death-1 (PD-1) antagonist for treating such CrPC patients.

SUMMARY OF THE INVENTION

The inventors have found that the high amplification and/or expression level of selective dipeptidyl peptidases and programmed death ligand-1 (PDL-1) or CD274 is a predictive factor of the response to combination therapies in patients with castration resistant prostate cancer (CrPC), as shown by correlating amplification and/or expression level of selective dipeptidyl peptidases and programmed death ligand-1 (PDL-1) or CD274 in the biological sample prior to the initiation of the therapy with the risk of early progression. Therefore, high amplification and/or expression level of selective dipeptidyl peptidases and programmed death ligand-1 (PDL-1) or CD274 can predict the likelihood of positive clinical response in patients after receiving the combination therapy comprising a selective dipeptidyl peptidase inhibitor and a PD-1 axis antagonist.

These findings support the use of amplification and/or expression level of selective dipeptidyl peptidases and programmed death ligand-1 (PDL-1) or CD274 as a predictive marker for detection, diagnosis, disease monitoring and prediction of response in patients with castration resistant prostate cancer (CrPC) who are susceptible to respond to the combination therapy (the selective dipeptidyl peptidase inhibitor and the PD-1 axis antagonist).

In principal aspect, the present invention provides a diagnostic and prognostic method for predicting the effectiveness of treatment of a castration resistant prostate cancer patient with a selective dipeptidyl peptidase inhibitor and a PD-1 axis antagonist. More particularly, the present invention provides a diagnostic and prognostic method for predicting the effectiveness of treatment of CrPC patients who have been progressed to the neuroendocrine form of prostate cancer (NEPC) with the selective dipeptidyl peptidase inhibitor and the PD-1 axis antagonist.

In one aspect, the present invention includes a method of stratification of castration resistant prostate cancer (CrPC) patients based on the determination of high or over amplification and/or expression of selective dipeptidyl peptidases and programmed death ligand-1 (PDL-1) or CD274 in the patient's biological sample and serves as an effective or sensitive prognostic or predictive method.

In another aspect, the present invention provides a computational approach for identifying a cancer patient segment in a dataset comprising:
 a) receiving a dataset of a biological sample from the cancer patient;
 b) determining/analyzing the amplification arid/or expression level of the genes including selective dipeptidyl peptidases consisting of DPP-8, DPP-9 or FAP, and programmed death ligand-1 (PDL-1) or CD274 in the dataset from the biological sample of the cancer patient; and,
 c) identifying the cancer patient segment in the dataset, wherein the amplification and/or expression level of the selective dipeptidyl peptidases comprising DPP-8, DPP-9 or FAP and the programmed death ligand-1 (PDL-1) or CD274 exceeds a predetermined threshold level.

In some aspect, the level of amplification and/or expression of selective dipeptidyl peptidases and programmed death ligand-1 (PDL-1) or CD274 is determined by using an amplification assay or a hybridization assay. In some instances, the amplification assay is a probe-based quantitative amplification assay, such as a TaqMan® assay. In some embodiments, the level of amplification and/or expression of selective dipeptidyl peptidases and programmed death ligand-1 (PDL-1) or CD274 ligand is determined using an immunoassay, immunohistochemistry, northern blotting, western blotting, Polymerase chain reaction (PCR), In situ hybridization (ISH/FISH), a whole genomic sequencing, a whole proteomic sequencing, quantitative real-time polymerase chain reaction (q-RT-PCR) and RNA sequencing or mass spectrometry.

In specific aspect, the present invention provides a method of prognosing castration resistant prostate cancer in a subject; said method comprising:
 (a) determining in a subject amplification and/or expression level of the genes including selective dipeptidyl peptidases consisting of DPP-8, DPP-9 or FAP and programmed death ligand-1 (PDL-1) or CD274 on a prognostic panel;
 (b) comparing the determined amplification and/or expression level of the genes including dipeptidyl peptidase consisting of DPP-8, DPP-9 or FAP and programmed death ligand-1 (PDL-1) or CD274 to a predetermined threshold level; and,
prognosing a case of castration resistant prostate cancer if the determined amplification and/or expression level is higher than or exceeds the predetermined threshold level.

In a specific aspect, the present invention provides a method for selecting a subject with castration resistant prostate cancer for a combination therapy comprising a selective dipeptidyl peptidase inhibitor and a PD-1 axis antagonist, said method comprising:
 (a) obtaining a biological sample from the subject with castration resistant prostate cancer;
 (b) determining the amplification and/or expression level of the genes including selective dipeptidyl peptidases consisting of DPP-8, DPP-9 or FAP and programmed death ligand-1 (PDL-1) or CD274 in the biological sample obtained from the subject; and
 (c) selecting the subject as a suitable candidate for the said therapy is based on an assessment that the amplification and/or expression level of selective dipeptidyl peptidases consisting of DPP-8, DPP-9 or FAP and programmed death ligand-1 (PDL-1) or CD274 higher or exceeds than a predetermined threshold level.

In another aspect, the present invention provides a method for determining likelihood that a therapy involving administration of a selective dipeptidyl peptidase inhibitor and a PD-1 axis antagonist to a subject afflicted with castration resistant prostate cancer (CrPC) provides a therapeutic benefit to the subject which comprises:
 (a) determining the amplification and/or expression level of the genes including selective dipeptidyl peptidases consisting of DPP-8, DPP-9 or FAP and programmed death ligand-1 (PDL-1), or CD274 in a biological sample obtained from the subject who is receiving the said therapy;
 (b) comparing the amplification and/or expression level of the genes including selective dipeptidyl peptidases consisting of DPP-8, DPP-9 or FAP and programmed death ligand-1 (PDL-1) or CD274 so obtained from the subject after receiving the said therapy to a predetermined threshold level of expression of respective genes in the biological sample of subjects who had a lack of therapeutic benefit from such a therapy;
wherein, there is a likelihood that the therapy will provide the therapeutic benefit to the subject if the level of amplification and/or expression determined in step a) is less than the predetermined threshold level of amplification and/or expression.

BRIEF DESCRIPTION OF THE DRAWING

FIG. 1: Oncoprint summary showing distinct genetic alterations in candidate genes of genomic signature (DPP-8/DPP-9/FAP) and PDL-1 in 'Neuroendocrine Prostate Cancer (Trento/Cornell/Broad 2016)' study from cBioPortal. Each patient is represented by a bar and frequency of genetic alterations as percentage cBioPortal version 1.4.3.

DETAILED DESCRIPTION OF THE INVENTION

I. Abbreviation(s)

As used herein, the following abbreviations have the following meanings:
ALK: Anaplastic lymphoma kinase
CCD: Charge-coupled device
CrPC: Castration-resistant prostate cancer
CNV: Copy number variation
CNA: Copy number alteration
ctDNA: Circulating tumor DNA
CrPC-NE: Castration-resistant prostate cancer-Neuroendocrine
DAPI: 4',6-diamidino-2-phenylindole
DNA: Deoxyribonucleic acid
DPP: Dipeptidyl peptidase
DPP-8: Dipeptidyl peptidase 8

DPP-9: Dipeptidyl peptidase 9
FACS: Fluorescence-activated cell sorting
FAP: Fibroblast activation protein
FFPE: Fresh-frozen or formalin fixed paraffin-embedded
FPKM: Fragments per kilobase of exon per million reads
FISH: Fluorescence in situ hybridization
GCSF: Granulocyte-colony stimulating factor
GM-CSF: Granulocyte-macrophage colony-stimulating factor
IFN: Interferon
IL: Interleukin
i.p.: Intraperitoneal
ISH: In situ hybridization
IHC: Immunohistochemistry
KLH: Key hole limpet haemocyanin
MDSCs: Myeloid-derived suppressor cells
NK: Natural killer
NEPC: Neuroendocrine prostate cancer
PBS: Phosphate buffered saline
PBMCs: Peripheral Blood Mononuclear Cells
PCR: Polymerase chain reaction
PD-1: Programmed Cell Death 1
PDL-1: Programmed Cell Death Ligand 1
PDL-2: Programmed Cell Death Ligand 2
p.o.: Per oral
PTEN: Phosphatase and tensin homolog
QD: Once daily
q-RT-PCR: Quantitative real-time polymerase chain reaction
TIL: Tumor infiltrating lymphocytes
TNF: Tissue necrosis factor

II. Definitions

The term "prostate cancer" includes but not limited to neuroendocrine prostate cancer (NEPC), castration resistant prostate cancer (CrPC), castration resistant prostate cancer-Neuroendocrine (CrPC-NE), hormone refractory prostate cancer, acinar adenocarcinoma, ductal adenocarcinoma, non-hormone refractory prostate cancer, transitional cell (or urothelial) cancer, squamous cell cancer or prostate carcinoid and/or sarcomas and the like.

The term "castration resistant prostate cancer" or "CrPC" includes but not limited to castration resistant prostate cancer, small cell cancer, large cell cancer, neuroendocrine prostate cancer (NEPC), castration resistant prostate cancer-neuroendocrine (CrPC-NE), and castration resistant prostate cancer (CrPC) treated with abiraterone and/or Enzalutamide.

The term "subject" includes human or patient and used interchangeably means any animal, including mammals, such as mice, rats, other rodents, rabbits, dogs, cats, swine, cattle, sheep, horses, or primates. In certain embodiments, the subject is a human, e.g., a human suffering from, at risk of suffering from, or potentially capable of suffering from cancers.

The terms "treating", "preventing", "reducing" or "treatment," as used herein refer to curative therapy, prophylactic therapy, and preventative therapy.

The terms "to detect prostate cancer", "diagnosis" or "prognosis" includes judgment, diagnosis or preliminary diagnosis of whether a test subject has prostate cancer, and includes judgment, diagnosis or preliminary diagnosis of whether a test subject who does not actually suffer from a prostate cancer or has a risk of suffering from prostate cancer in the future. The term "diagnosis" also includes using the results of an assay of amplification and/or expression level including but not limited to Polymerase chain reaction (PCR), In situ hybridization (ISH/FISH), Northern blotting and Western blotting, a whole genomic sequencing, a whole proteomic sequencing or RNA sequencing.

The term "therapeutically effective amount" can be used interchangeably with "therapeutically effective dose," or "effective amount," and it refers to an amount sufficient to produce the desired effect. Therapeutically effective amount is sufficient to cause an improvement in a clinically significant condition of the subject.

"Dipeptidyl peptidase (DPP)" refers to a class of enzymes encoded by DPP gene (classified under EC 3.4.14). There are 9 types of DPP genes are known to date. These include Cathepsin C (DPP-1), DPP-2, DPP-3, DPP-4, DPP-6, DPP-7, DPP-8, DPP-9 and DPP-10. The DPP also includes fibroblast activation protein (FAP).

The terms "selective dipeptidyl peptidases" and "DPP-8/DPP-9/FAP" refer to a subset of DPP enzymes or genes containing one or more of DPP-8, DPP-9 and FAP.

The term "selective dipeptidyl peptidase inhibitor" also termed a DPP8/DPP9/FAP inhibitor is a small molecule or antibody that inhibits one or more of DPP8, DPP9 and FAP. This term refers to dipeptidyl peptidase 8 inhibitors, dipeptidyl peptidase 9 inhibitors, dipeptidyl peptidase 8 and dipeptidyl peptidase 9 inhibitors, FAP inhibitors, dipeptidyl peptidase 8 and dipeptidyl peptidase 9 and FAP inhibitor.

In some aspects the selective dipeptidyl peptidase inhibitor is talabostat or a pharmaceutically acceptable salt thereof. As used herein, "pharmaceutically acceptable salt" refers to a salt known to be non-toxic and commonly used in the pharmaceutical literature. Typical inorganic acids used to form such salt include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyl alkandioic acids, aromatic acids, aliphatic (mesylate) and aromatic sulfonic acids may also be used. A preferred salt is the mesylate salt.

As used herein, "expression level" in a subject, for example, of the selective dipeptidyl peptidase or programmed cell death ligand-1 (PDL-1) transcript, refers to an amount of transcript, such as DPP-8, DPP-9, FAP or PDL-1 RNA, in the subject's undiagnosed biological sample. The expression level may be compared to a threshold expression level to determine a status of the sample. A subject's expression level can be an absolute value (e.g, number of copies/ml, nanogram/ml or microgram/ml), a relative value (e.g., relative intensity of signals; a percent or "fold" or "fold-change" increase), a value that has an upper or a lower limit, a range of values, an average value, a median value, a mean value, or a value as compared to a particular control or baseline value.

As used herein, "about" means about plus or minus 10% of the indicated value.

As used herein, "amplification level" in a subject, for example, of the selective dipeptidyl peptidase or programmed cell death ligand-1 (PDL-1) transcript, refers to an amount of transcript, such as DPP-8, DPP-9, FAP or PDL-1 protein, in the subject's undiagnosed biological sample. The amplification level may be compared to a threshold amplification level to determine a status of the sample. A subjects amplification level can be an absolute value (e.g., number of copies/ml, nanogram/ml or microgram/ml), a relative value (e.g., relative intensity of signals; a percent or "fold" or "fold-change" increase), a value that has an upper or a lower limit, a range of values, an average value, a median value, a mean value, or a value as compared to a particular control or baseline value.

As used herein, "predetermined threshold value" can be used interchangeably with "predetermined threshold level". Predetermined threshold value refers to the amplification and/or expression level of the selective dipeptidyl peptidase or programmed cell death ligand-1 (PDL-1) or CD274 genes in the biological samples obtained by examinations of subjects or samples collected from subjects. The predetermined threshold value can be an absolute value (e.g., number of copies/ml, nanogram/ml or microgram/ml), a relative value (e.g., relative intensity of signals; a percent or "fold" or "fold-change" increase), a value that has an upper or a lower limit, a range of values, an average value, a median value, a mean value, or a value as compared to a particular control or baseline value. It can be a threshold value or a range. It can be based on a large number of biological samples, such as from population of subjects of the chronological age matched group, or based on a pool of samples including or excluding the sample to be tested or the subject which respond to the combination therapy or which did not respond to the combination therapy. When, the amplification and/or expression value is higher than the predetermined threshold value in a biological sample is indicative that said subject likelihood of getting positive clinical response from said combination therapy of the selective dipeptidyl peptidase inhibitor and the PD-1 axis antagonist.

III. Gene(s): The Genes Related to the Present Invention are Described Below Selective Dipeptidyl Peptidase (DPP) Gene:

The selective DPP of the present invention includes specifically DPP-8, DPP-9 or FAP. The term genes of selective DPP includes DPP-8/DPP-9/FAP individually or combinedly.

Programmed Cell Death-1 (PD-1) Gene:

PD-1 is a member of the immunoglobulin gene family and several studies demonstrated how it is expressed on the surface of activated T cells, activated B cells, regulatory T-Cells and natural killer (NK).

It has two ligands, PDL-1 and PDL-2 and when the T-Cell receptor PD-1 binds to its ligands on antigen presenting cells (APC), the inhibitory pathway is activated leading to the suppression of effector T-cell response.

PDL-1 (B7-H1 or CD274) is a cell surface glycoprotein and it has been demonstrated how it is basically express in sites like placenta tonsil and retina, all implicated in immune tolerance mechanism; the protein can also be expressed on hematopoietic cells (dendritic, myeloid, T and B cells), non-hematopoietic cells and on tumor cell.

PDL-2 (B7-DC or CD273) expression is induced more strongly by interleukin 4 (IL-4) than IFN (Interferon) gamma and it is mainly expressed on activated dendritic cells and some macrophages.

IV. Biological Sample

The biological sample includes tumour cells and associated stromal cells/fibroblasts/macrophages and other immune related cells (e.g. tumour infiltrating lymphocytes usually CD8+ T cells, MDSCs, T regs), NK cells, circulating tumour DNA (ctDNA) and circulating tumour cells (etc.).

V. Combination Therapy:

The combination therapy related to the present invention is described below. The combination comprises a selective dipeptidyl peptidase inhibitor and a PD-1 axis antagonist.

a) Selective Dipeptidyl Peptidase (DPP) Inhibitor:

The dipeptidyl peptidase (DPP)-like gene family is a family of molecules which have related protein structure and function. The gene family includes the following molecules: DPPIV (CD26), dipeptidyl amino-peptidase-like protein 6 (DPP-6), dipeptidyl amino peptidase-like protein 8 (DPP-8), dipeptidyl amino-peptidase-like protein 9 (DPP-9), and fibroblast activation protein (FAP). The selective dipeptidyl peptidase inhibitor includes FAP and DPP-8/DPP-9 inhibitors individually or combinedly. With respect to oncology, the current notion for the DPPs (particularly FAP and DPP-8/DPP-9) are of importance to talabostat mechanism of action.

DPP-8, DPP-9 and FAP inhibitor known in the market is talabostat (PT-100, Val-boro-pro). FAP monoclonal antibody known in the market is Sibrotuzumab.

Talabostat has a CAS registration number of 149682-77-9. In some aspect, the free base may be used. The salt form may be talabostat mesylate. Talabostat mesylate has a CAS registration number of 150080-09-4. Talabostat is in racemic form or an enantiomer having R or S configuration. Talabostat can exist as both linear and cyclic forms.

FAP inhibitors include but not limited to, such as ARI-3099 (N-(pyridine-4-carbonyl)-d-Ala-boroPro) as disclosed in Sarah E. Poplawski et al., 2013, Vol. 56(9), Page no. 3467-3477; ARI-3996 as disclosed in U.S. Patent Appl. Publication No. 20140255300; MIP-1231 (MIP-1232 or MIP-1233) as disclosed in U.S. Patent Appl. Publication No, 20100098633; (4-quinolinoyl)-glycyl-2-cyanopyyrolidines as disclosed by Koen Jansen et al., 2013, Vol. 4 (5), Page no. 491-496; (2S)-1-(2-(1-Napthoylamino)acetyl)pyrroline-2-carbonitrile as disclosed in U.S. Pat. No. 8,183,280; (S)-A-(2-(2-cyano-4,4-difluoropyrrolidin-1-yl)-2-oxoethyl)-1-naphthamide and other related derivatives as disclosed in WO2013107820; (2S)-1-((2S)-2-(2-Methoxybenzoylamino)-3-methylpentanoyl) pyrrolidine-2-carbonitrile and other related derivatives as disclosed in U.S. Patent Appl. Publication No. 20120053222; Ac-Gly-BoroPro as disclosed by Conrad Yap Edosada et al. 2006, Vo. 281(11) Page no. 7437-7444; Substituted 4-carboxylmethyl pyroglutamic acid diamides as disclosed in Ting-yueh Tsai et al., 2010, Vol. 53(18), 6572-6583; GEH200200 as disclosed by P. Iveson et al., 2014, Vol. 41(7), 620; UAMC-1110 as disclosed in U.S. Pat. No. 9,346,814; some FAP inhibitors also disclosed in WO2002038590, U.S. Pat. Nos. 7,399,869; 7,998,997.

Other patents that disclose the FAP-α antibody such as U.S. Pat. No. 8,568,727 (assigned to Boehringer Ingelheim. International Gmbh), E.P. Patent No. 1,268,550 (assigned to Boehringer Ingelheim. International Gmbh), U.S. Pat. No. 8,999,342 (assigned to Ludwig Institute for Cancer Research Ltd), U.S. Pat. No. 9,011,847 (assigned to Roche Glycart). Bispecific antibodies of FAP with DR-5 is disclosed in U.S. Patent Appl. Publication No. 20140370019 and 20120184718; Chimeric antigen receptor and FAP combination is disclosed in U.S. Patent Appl. Publication No. 20140099340.

F11-24 antibody is a mouse monoclonal antibody targeting against FAP. Anti-FAP-α antibody include antibodies which are raised in mouse against epitope of Key hole limpet haemocyanin (KLH) conjugated synthetic peptide between 15-41 amino acids from the N-terminal region; Leu26-Asp760 amino acid; and 525-625 amino acid.

(PPQFDRSKKYKLIQVYGGPCSQSVRSVFAVNWISYLASKEGNIVIALVD

GRGTAFQGDKLLYAVYRKLGVYEVEDQITAVRKFIEMGFIDEKRIAIWGW

S - (SEQ ID NO: 1)).

Similarly, anti-FAP antibody include antibodies which are raised in rabbit against the epitope of N-terminus of human fibroblast activation protein, alpha of 57-73 amino acid with sequence FFPNWISGQEYLHQSAD (SEQ ID NO: 2); 26-280 amino acid; 95-337 amino acid; 300-380 amino acid; 331-380 amino acids from the Internal region of human FAP-1; 350-400 amino acid; KLH-conjugated synthetic peptide of 396-426 amino acid, Lys366 amino acid; Ile523-Asp760 amino acid of human seprase expressed in E. coli; 525-625 amino acid; 544-599 amino acid; Gly542-Asp761 amino acid; 652-701 amino acid; C-terminal region of Human FAP of immunogen sequence.

(SEQ ID NO: 3)
SWEYYASVYTERFMGLPTKDDNLEHYKNSTVMARAEYFRNVDYLLIHGT

A;

(SEQ ID NO: 4)
ERCQYYTASFSDYAKYYALVCYGPGIPISTLHDGRTDQEIKILEENKELE

NALKNIQLPKEEIKKLEVDEITLWYKM.

In other aspects, the anti-FAP antibody may be a nanobody. Nanobody technology was developed from the discovery that antibodies from camels and llamas (Camelidae, camelids) have heavy chains but no light chains. The antigen-binding site of such antibodies is one single domain, and may be referred to as VHH. See, e.g., U.S. Pat. Nos. 5,800,988 and 6,005,079 and International Application Publication Nos. WO 94/04678, WO 94/25591 and EP 2673297 which are incorporated by reference.

DPP-8/DPP-9 specific inhibitors are (2S,3R)-2-amino-1-(isoindolin-2-yl)-3-methylpentan-1-one (allo-Ile-isoindoline (UAMC00132); (S)-2,6-diamino-1-(isoindolin-2-yl) hexan-1-one (Lys-isoindoline (UAMC00071); IG244 (PTX-1210; (S)-2-Amino-4-{4-[bis-(4-fluorophenyl)-methyl]piperazin-1-yl}-1-(1,3-dihydro-isoindol-2-yl)-butane-1,4-dione); PTX-1200 (cyclohexyl glycine-isoindoline); (2S)-2-Amino-4-(4-((4-chlorophenyl)(phenyl)methyl)pipe-razin-1-yl)-1-(5-fluoroisoindo-lin-2-yl)butane-1,4-dione bis-(2,2,2-trifluoroacetate); (2S)-2-Amino-4-(4-((4-chlorophenyl)(phenyl)methyl)pipe-razin-1-yl)-1-(isoindolin-2-yl)butane-1,4-dione bis(2,2,2-tri-fluoroacetate); (S)-2-Amino-4-((S)-4-(bis(4-fluorophenyl)methyl)-3-methyl-piperazin-1-yl)-1-(isoindolin-2-yl)butane-1,4-dione Bis(2,2,2-tri-fluoroacetate); (2S)-2-Amino-4-((3R)-4-((3-fluorophenyl)(4-fluorophenyl)-methyl)-3-methylpiperazin-1-yl)-1-(isoindolin-2-yl)butane-1,4-dione Bis (2,2,2-trifluoroacetate, SUMO1 EIL Peptide (as disclosed in U.S. Patent Appl. Publication No. 20150266922).

b) PD-1 axis antagonist:

PD-1 axis antagonist includes PD-1 antagonist (for example anti-PD-1 antibody), PDL-1 antagonist (for example anti-PDL-1 antibody) and PDL-2 antagonist (for example anti-PDL-2 antibody).

As used herein, the terms "Programmed Death 1," "Programmed Cell Death 1," "Protein PD-1," "PD-1," PD1," "PDCD1," "hPD-1" and "hPD-1" are used interchangeably, and include variants, isoforms, species homologs of human PD-1, and analogs having at least one common epitope with human PD-1. The complete human PD-1 sequence can be found under GenBank Accession No. U64863. In particular aspects, the PD-1 antagonist binds the PD-1 protein of SEQ ID NO: 5 (uniprot ID Q15116).

As used herein, the terms "Programmed Cell Death 1 Ligand 1", "PDL-1", "PDL1", "PDCD1L1", "PDCD1LG1", "CD274", "B7 homolog 1", "B7-H1", "B7-H", and "B7H1" are used interchangeably, and include variants, isoforms, species homologs of human PDL-1, and analogues having at least one common epitope with human PDL-1.

The protein programmed death 1 (PD-1) is an inhibitory member of the CD28 family of receptors, that also includes CD28, CTLA-4, ICOS and BTLA.

Two ligands for PD-1 have been identified, PD-L1 and PD-L2, that have been shown to downregulate T cell activation upon binding to PD-1 (Freeman et al. (2000) J Exp. Med. 192: 1027-34; Latchman et al. (2001) Nat Immunol. 2:261-8; Carter et al. (2002) Eur. J Immunol 32:634-43). Both PD-L1 and PD-L2 are B7 homologs that bind to PD-1, but do not bind to other CD28 family members.

PD-1 antagonist of the invention binds to ligands of PD-1 and interfere with, reduce, or inhibit the binding of one or more ligands to the PD-1 receptor, or bind directly to the PD-1 receptor, without engaging in signal transduction through the PD-1 receptor. The PD-1 antagonist binds to one or more ligands of PD-1 (e.g., PD-L1 and PD-L2) and reduces or inhibits the ligand(s) from triggering inhibitory signal transduction through the PD-1. In one embodiment, the PD-1 antagonist binds directly to PDL-1, inhibiting or preventing PDL-1 from binding to PD-1, thereby blocking PD-1 inhibitory signal transduction.

In some embodiment, the antibodies interfering with PD-1 is an anti-PD-1 antibody or PD-1 antagonist (e.g., a human antibody, a humanized antibody, or a chimeric antibody).

Nivolumab (also known as Opdivo®, MDX-1106, MDX-1106-04, ONO-4538 or BMS-936558), is PD-1 antagonist described in U.S. Pat. No. 8,008,449 and WO2006/121168. Pembrolizumab (also known as Merck 3475, MK-3475, Lambrolizumab, Keytruda®, and SCH-900475) is a PD-1 antagonist described in U.S. Pat. No. 8,345,509 and WO2009/114335. Other PD-1 antagonist is disclosed in U.S. Pat. No. 8,609,089, US 20100028330, and/or US 20120114649.

Atezolimumab (MDPL3280A or YW243.55.S70) is a PDL-1 antagonist described in U.S. Pat. No. 8,217,149. MDX-1105 (also known as BMS-936559) is a PDL-1 antagonist described in WO2007/005874. Durvalumab (MED14736) is a PDL-1 antagonist described in WO2011/066389 and US2013/0034559. Avelumab (MSB0010718C) is PDL-1 antagonist described in US 20140341917. CA-170 is a PDL-1 antagonist described in WO2015033301 & WO2015033299.

AMP-224 (also known as B7-DCIg) is a PD-L2-Fc fusion soluble receptor described in WO2010/027827 and WO2011/066342.

The antibody or antigen binding fragment thereof, may be made using methods known in the art, for example, by a process comprising culturing a host cell containing nucleic acid encoding any of the previously described PD-1, PDL-1, or PDL-2 antagonist or antigen-binding fragment in a form suitable for expression, under conditions suitable to produce such antibody or fragment, and recovering the antibody or fragment.

In one embodiment, the PD-1 antagonist is selected from the group consisting of ANA011, AUNP-12, BGB-A317, KD033, pembrolizumab, MCLA-134, mDX400, MEDI00680, muDX400, nivolumab, PDR001, PF-06801591, REGN-2810, SHR-1210, STI-A1110, TSR-042, ANB011, 244C8, 388D4, TSR042 and XCE853 and combinations thereof. Preferably the PD-1 antagonist is Pembrolizumab and Nivolumab Anti-PD-1 antibody may be procured from BPS Biosciences and Bio X cell.

In one embodiment, the PDL-1 antagonist is selected from the group consisting of avelumab, BMS-936559, CA-170, durvalumab, MCLA-145, SP142, STI-A1011, STIA1012, STI-A1010, STI-A1014, A110, KY1003 and atezolimumab and combinations thereof. Preferably the PDL-1 antagonist is avelumab, durvalumab and atezolimumab.

In one embodiment, the PDL-2 antagonist is selected from the group consisting of AMP-224 and rHIgM12B7 and combinations thereof.

VI. Castration Resistant Prostate Cancer (CrPC):

Androgen deprivation is the mainstay of therapy for advanced prostate cancer, and this treatment leads to prostate-specific antigen (PSA) responses and clinical improvements in more than 90% of patients; however, this treatment is not curative, and most patients eventually become castrate resistant. The term 'castration-resistant prostate cancer' (CrPC) identifies a heterogeneous group of both symptomatic and asymptomatic patients with or without clinical metastases.

Castration resistant prostate cancer (CrPC) of the present invention includes but not limited to small cell cancer, large cell cancer, castration resistant prostate cancer, neuroendocrine prostate cancer (NEPC), castration resistant prostate cancer-neuroendocrine (CrPC-NE) and castration resistant prostate cancer (CrPC) pre-treated with Abiraterone and/or Enzalutamide.

In some embodiments, the CrPC patient is preferably suffering from neuroendocrine prostate cancer (NEPC).

In another embodiment, the CrPC patient is CrPC patient pre-treated with abiraterone and/or enzalutamide.

VII. Detecting Level of Selective Dipeptidyl Peptidases (DPP-8/DPP-9/FAP) and Programmed Death Ligand 1 (PDL-1)

The amplification and/or expression level of the genes are determined assessing the quantitative level of predictive markers {(mRNA/protein expression) or CNV/CNA (DNA/gene)}. The determination can be made using any well-established method. These methods include bioassays comprising an amplification assay, a hybridization assay, an immunoassay, an immunohistochemistry, a western blot, a northern blot, a whole genomic sequencing, a whole proteomic sequencing, RNA sequencing, mass spectrometry, a probe-based quantitative amplification assay, a polymerase chain reaction (PCR) and a quantitative real-time polymerase chain reaction (qRT-PCR).

In one embodiment of the present invention, the genes amplification and/or expression is determined for the diagnosis or prognosis of CrPC patients includes detecting the level of amplification and/or expression of selective dipeptidyl peptidase consisting of DPP-8, DPP-9 or FAP and the programmed death ligand-1 (PDL-1) or CD274.

In one embodiment of the present invention, the gene amplification and/or expression level is determined for the diagnosis or prognosis of CrPC patients pre-treated with abiraterone and/or enzalutamide includes detecting level of amplification and/or expression of selective dipeptidyl peptidase consisting of DPP-8, DPP-9 or FAP and the programmed death ligand-1 (PDL-1) or CD274.

In one embodiment of the present invention, the genes amplification and/or expression level is determined for the diagnosis or prognosis of CrPC patients un-treated with abiraterone and/or enzalutamide includes detecting level of amplification and/or expression of selective dipeptidyl peptidase consisting of DPP-8, DPP-9 or FAP.

VIII. Establishing a Predetermined Threshold Level:

In order to establish a predetermined threshold level for practicing the method of this invention, a reference population of subjects can be used, wherein the reference population, typically a normal population, i.e. a population of the subjects having not diagnosed for cancer or the population of the subjects having diagnose for the cancer, is selected and useful statistical characteristics from the reference population are determined and can be used. In some embodiments, a population of prostate cancer patients receiving a therapy other than a selective DPP inhibitor and a PD-1 axis antagonist or another molecular targeted therapy can be used. In some embodiments, the prostate cancer patients in the reference group may receive a therapy other than selective DPP inhibitor and PD-1 axis antagonist or another molecular targeted therapy, in combination with chemotherapy, radiation therapy and/or surgical resection of the tumor. In other embodiments, the reference population includes subjects who do not have prostate cancer. In yet other embodiments, the reference population includes subjects who have prostate cancer and are not receiving targeted therapy. In yet other embodiments, the reference population includes subjects who have prostate cancer and are receiving combination therapy of selective DPP inhibitor and PD-1 axis antagonist. These patients are within the appropriate parameters, if applicable, for the purpose of screening for and/or monitoring cancer using the methods of the present invention. Optionally, the patients are of same gender, similar age, or similar ethnic background.

In yet another embodiment, the reference population is the same subject who is suffering from the castration resistant prostate cancer and the normal tissue is taken from this CrPC patient to establish a predetermined threshold level.

The status of the selected patients is confirmed by well established, routinely employed methods including but not limited to general physical examination of the individuals and general review of their medical history.

Furthermore, the selected group of patients must be of a reasonable size, such that the average level/amount/concentration of human DPP-8, DPP-9 or FAP and PDL-1 polynucleotide (mRNA) or DPP-8, DPP-9 or FAP and PDL-1 protein or DPP-8, DPP-9 or FAP and PDL-1 amplification of a gene in the sample obtained from the group can be reasonably regarded as representative of the normal or average level among this population of patients.

Once a threshold value for the DPP-8, DPP-9 or FAP and PDL-1 polynucleotide (mRNA) or DPP-8, DPP-9 or FAP and PDL-1 protein is established based on the individual values found in each subject of the selected group, wherein the selected group can be based on a large number of biological samples, such as from population of subjects of the chronological age matched group, or based on a pool of samples including or excluding the sample to be tested or the subject which respond to the combination therapy or which did not respond to the combination therapy, this threshold value can be considered as predetermined threshold level. A standard deviation is also determined during the same process. In some cases, separate threshold level may be established for separately defined groups having distinct characteristics such as age, gender, or ethnic background.

The predetermined threshold level for the present invention includes the predetermined threshold level of amplification and/or expression. For amplification, the predetermined threshold level is 2 (as per in-silico experiments in Example 2-5), whereas, in case of mRNA expression the predetermined threshold level is an average or median established based on the individual values found in each subject. Further, the predetermined threshold level may vary depending upon biological sample purity and ploidy.

IX. Selecting a Subject for Combination Therapy Comprising a Selective Dipeptidyl Peptidase Inhibitor and PD-1 Axis Antagonist According to the methods described herein, the amplification and/or expression level of DPP-8/DPP-9/FAP and PDL-1 in the patient's biological sample is compared to the predetermined threshold level. In some embodiments, the amplification and/or expression level of DPP-8/DPP-9/FAP and PDL-1 is deemed "high" if it is at least 1, 2, 3, 4, 5, 10, 15, 20 or more standard deviations greater than the reference value subjects (threshold level). In other embodiments, the amplification and/or expression level of DPP-8/DPP-9/FAP and PDL-1 is "low" if it is at least 1, 2, 3, 4, 5, 10, 15, 20 or more standard deviations lower than the reference or threshold level.

If amplification and/or expression level in a biological sample from the test subject is significantly higher {e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more higher) than the predetermined threshold level, this would indicate, e.g., the test subject is selected for a combination therapy comprising selective dipeptidyl peptidase inhibitor and PD-1 axis antagonist. If amplification and/or expression level in a sample from the test subject is significantly lower (e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more higher) than the predetermined threshold level, this would indicate, e.g., the test subject is not selected for a combination therapy comprising a selective dipeptidyl peptidase inhibitor and a PD-1 axis antagonist.

As described herein, the present invention includes a method of selecting a subject for combination therapy comprising a selective dipeptidyl peptidase inhibitor and a PD-1 axis antagonist; the method comprising; obtaining a biological sample from the subject with CrPC; determining the amplification and/or expression level of the genes including selective dipeptidyl peptidases consisting of DPP-8, DPP-9 or FAP and programmed death ligand-1(PDL-1) or CD274 in the biological sample obtained from the subject; and selecting the combination therapy for the treatment if the amplification and/or expression level in the biological sample exceeds a predetermined threshold level.

In another embodiment, the present invention includes a method of selecting a subject for combination therapy comprising a selective dipeptidyl peptidase inhibitor and a PD-1 axis antagonist; the method comprising; obtaining a biological sample from the subject with prostate cancer; determining the amplification and/or expression level of the genes including dipeptidyl peptidases consisting of DPP-8, DPP-9 or FAP and programmed death ligand-1 (PDL-1) or CD274 in the biological sample obtained from the subject; and selecting the combination therapy for the treatment if the amplification and/or expression level in the biological sample exceeds a predetermined threshold level.

In yet another embodiment, the present invention includes a method of selecting a subject for combination therapy comprising a selective dipeptidyl peptidase inhibitor, abiraterone and/or enzalutamide; the method comprising; obtaining a biological sample from the subject with CrPC; determining the amplification and/or expression level of the genes including selective dipeptidyl peptidases consisting of DPP8, DPP 9 or FAP; in the biological sample obtained from the subject; and selecting the said combination therapy for the treatment if the amplification and/or expression level in the tissues sample exceeds a predetermined threshold level.

X. Patient Population

The present invention may be used to diagnose or prognosis in a subject having CrPC. Additionally, the present invention may also be used to select a patient having CrPC, preferably CrPC-NE and said patient possess likelihood of a good prognosis or a positive clinical response to a combination comprising a selective dipeptidyl peptidase inhibitor and a PD-1 axis antagonist. Further, the present invention may also be used to treat a subject having CrPC. The subject may include but not limited to a subject suffering from CrPC comprises neuroendocrine prostate cancer (NEPC), castration resistant prostate cancer-neuroendocrine (CrPC-NE), castration resistant prostate cancer (CrPC) previously treated with abiraterone and/or enzalutamide or the like. The subject may also include subject suffering from castration resistant prostate cancer (CrPC) including but not restricted to small cell cancer, large cell cancer, neuroendocrine prostate cancer (NEPC) which are treated or untreated with abiraterone and/or enzalutamide. Preferably, the patients suffering from neuroendocrine prostate cancer is selected for the combination therapy.

Further, the present invention may also be used to diagnose or prognosis in a subject having prostate cancer. Additionally, the present invention may also be used to select a subject having prostate cancer and said patient possess likelihood of a good prognosis or a positive clinical response to a combination comprising a selective dipeptidyl peptidase inhibitor and a PD-1 axis antagonist. Further, the present invention may also be used to treat a subject having prostate cancer. The subject may include but not limited to a subject suffering from prostate cancer comprises neuroendocrine prostate cancer (NEPC), castration resistant prostate cancer-neuroendocrine (CRPC-NE), castration resistant prostate cancer (CRPC), hormone refractory prostate cancer, acinar adenocarcinoma, ductal adenocarcinoma, non-hormone refractory prostate cancer, transitional cell (or urothelial) cancer, squamous cell cancer or prostate carcinoid and/or sarcomas and the like. The subject may also include subject suffering from castration resistant prostate cancer (CrPC) including but not restricted to small cell cancer, large cell cancer, neuroendocrine prostate cancer (NEPC) which are treated or untreated with abiraterone and/or enzalutamide.

In addition to above, the present invention may also be used to diagnose or prognosis in a subject having abiraterone and/or enzalutamide resistant CrPC. The present invention may also be used to select a subject having abiraterone and/or enzalutamide resistant CrPC and said patient possess likelihood of a good prognosis or a positive clinical response to a combination comprising a selective dipeptidyl peptidase inhibitor and a PD-1 axis antagonist. Further, the present invention may also be used to treat a subject having abiraterone and/or enzalutamide resistant CrPC. The subject may also include subject suffering from abiraterone and/or enzalutamide resistant CrPC including but not restricted to abiraterone and/or enzalutamide resistant small cell cancer, large cell cancer and neuroendocrine prostate cancer (NEPC). In addition to above, the present invention may also be used to diagnose or prognose a subject having CrPC but not treated with abiraterone and/or enzalutamide. The present invention may also be used to select a subject having CrPC and said patient possess likelihood of a good prognosis or a positive clinical response to a combination comprising a selective dipeptidyl peptidase inhibitor, abiraterone and/or enzalutamide. Further, the present invention may also be used to treat a subject with triple therapy comprising selective dipeptidyl peptidase inhibitor with abiraterone and/or enzalutamide.

XI. Method of Prognosis of Prostate Cancer

As described herein, the present invention includes a method of prognosing CrPC in a subject; the method includes determining the amplification and/or expression level of the genes including selective dipeptidyl peptidases consisting of DPP-8. DPP-9 or FAP and programmed death ligand-1 (PDL-1) or CD274; comparing the determined amplification and/or expression level of the genes including selective dipeptidyl peptidases consisting of DPP-8, DPP-9 or FAP and programmed death ligand-1 (PDL-1) or CD274 to a predetermined threshold level; and prognosing a case of CrPC if the determined amplification and/or expression level exceeds the predetermined threshold level.

In another embodiment, the present invention also discloses a method of prognosing prostate cancer in a subject; the method includes determining the amplification and/or expression level of the genes including selective dipeptidyl peptidases consisting of DPP-8, DPP-9 or FAP and programmed death ligand-1 (PDL-1) or CD274; comparing the determined amplification and/or expression level of the genes including selective dipeptidyl peptidases consisting of DPP-8, DPP-9 or FAP and programmed death ligand-1 (PDL-1) or CD274 to a predetermined threshold level; and prognosing a case of prostate cancer if the determined amplification and/or expression level exceeds the predetermined threshold level.

In yet another embodiment, the present invention includes a method of prognosing CrPC untreated with abiraterone and/or enzalutamide in a subject; the method includes determining the amplification and/or expression level of the genes including selective dipeptidyl peptidases consisting of DPP-8, DPP-9 or FAP; comparing the determined amplification and/or expression level of the genes including selective dipeptidyl peptidases consisting of DPP-8, DPP-9 or FAP to a predetermined threshold level; and prognosing a case of CrPC untreated with abiraterone and/or enzalutamide if the determined amplification and/or expression level exceeds the predetermined threshold level.

XII. Method of Treating

The present invention provides a method of treating a subject with CrPC by administering to the subject therapeutically effective amount of a selective dipeptidyl peptidase inhibitor and a PD-1 axis antagonist.

In one embodiment, the PD-1 axis antagonist is administered at a dose from about 0.01 to 30 mg/kg, preferably 0.1 to 20 mg/kg, more preferably 1 to 10 mg/kg. In one specific embodiment, the PD-1 axis antagonist is Nivolumab and Pembrolizumab.

In certain embodiments, the PD-1 axis antagonist is administered in a dose of about 0.01 mg/kg, about 0.05 mg/kg, about 0.1 mg/kg, about 0.2 mg/kg, about 0.3 mg/kg, about 0.5 mg/kg, about 0.7 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 15 mg/kg. about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg or about 30 mg/kg. In certain embodiments, the PD-1 axis antagonist is administered by injection (e.g., subcutaneously or intravenously) at a dose of about 0.01 mg/kg to 30 mg/kg, e.g., about 0,1 mg/kg to 20 mg/kg, about 1 mg/kg to 10 mg/kg, about 1 mg/kg to 5 mg/kg, or about 1 to 3 mg/kg.

In other embodiments, each dose of the PD-1 axis antagonist is administered at 0.1, 0.3, 1, 3, 6, 10, 15 or 20 mg/kg body weight. In preferred embodiments, each dose of the PD-1 axis antagonist is administered at 0.3, 1, 2, 3 or 10 mg/kg. In more preferred embodiments, the PD-1 axis antagonist is administered at a dose of 2 mg/kg on every three weeks (Keytruda®) or 3 mg/kg on every two weeks (Opdivo®) or 1200 mg on every three weeks (Tecentriq®).

In one embodiment, the dose of a selective dipeptidyl peptidase inhibitor may vary from about 0.001 mg/kg to 10 mg/kg, preferably 0.001 mg/kg to 3 mg/kg, more preferably about 0.001 mg/kg to 2 mg/kg. The dose of talabostat or a pharmaceutically acceptable salt thereof may vary from about 0.001 mg/kg to 1 mg/kg, preferably 0.001 mg/kg to 0.05 mg/kg, more preferably about 0.001 mg/kg to 0.035 mg/kg. In one specific embodiment, the dipeptidyl peptidase inhibitor is talabostat or a pharmaceutically acceptable salt thereof, preferably talabostat mesylate.

In certain embodiments, the selective dipeptidyl peptidase inhibitor (for example talabostat or a pharmaceutically acceptable salt thereof) is administered in a dose of 0.001 mg/kg, 0.002 mg/kg, 0.003 mg/kg. 0.004 mg/kg, 0.005 mg/kg, 0.006 mg/kg, 0.007 mg/kg, 0.008 mg/kg. 0.009 mg/kg, 0.010 mg/kg, 0.012 mg/kg, 0.013 mg/kg, 0.014 mg/kg, 0.020 mg/kg, 0.025 mg/kg. 0.030 mg/kg and 0.035 mg/kg. In preferred embodiments, each dose of the selective dipeptidyl peptidase inhibitor is administered at 0.002 mg/kg, 0.003 mg/kg, 0.004 mg/kg, 0.005 mg/kg, 0.006 mg/kg, 0.007 mg/kg, 0,009 mg/kg. 0.01 mg/kg, 0.013 mg/kg and 0.014 mg/kg. In another embodiment, the dosage of the selective dipeptidyl peptidase inhibitor of the invention administered to prevent and/or treat a cancer associated with increased levels of DPP-8/DPP-9/FAP in a patient is a unit dose of about 0.001 mg/kg to about 10 mg/kg, 0.001 mg/kg to about 1 mg/kg, about 0.001 mg/kg to 0.05 mg/kg, about 0.001 mg/kg to 0.035 mg/kg, about 0.002 mg/kg to about 5 mg/kg, about 0.002 mg/kg to about 3 mg/kg, about 0.002 mg/kg to about 2 mg/kg, about 0.002 mg/kg to about 0.05 mg/kg, about 0.002 mg/kg to about 0.035 mg/kg, about 0.003 mg/kg to about 2.0 mg/kg, about 0.003 mg/kg to about 2.0 mg/kg, about 0.004 mg/kg to about 2.5 mg/kg, about 0.005 mg/kg to about 2.5 mg/kg, about 0.006 mg/kg to about 2.5 mg/kg, about 0.007 mg/kg to about 2.5 mg/kg, about 0.008 mg/kg to about 2.5 mg/kg, about 0.009 mg/kg to about 2.5 mg/kg, about 0.010 mg/kg to about 1.5 mg/kg, about 0.011 mg/kg to about 1.5 mg/kg, about 0.012 mg/kg to about 1 mg/kg, about 0.013 mg/kg to about 1 mg/kg. Total daily dose of a selective dipeptidyl peptidase inhibitor may vary from about 100 mcg to 200 mg, preferably about 100 mcg to 50 mg, most preferably about 100 mcg to 10 mg. Total daily dose of talabostat may vary from about 50 mcg to 3 mg, preferably about 100 mcg to 2.5 mg, most preferably about 100 mcg to 2.0 mg.

In certain embodiments, each dose of the selective dipeptidyl peptidase inhibitor is administered at about 0.001 mg/kg, about 0.003 mg/kg, about 0.005 mg/kg, about 0.006 mg/kg, about 0.007 mg/kg, about 0.008 mg/kg, about 0.009 mg/kg, about 0.01 mg/kg, about 0.012 mg/kg, about 0.013 mg/kg, about 0.014 mg/kg, about 0.015 mg/kg, about 0.016 mg/kg, about 0.017 mg/kg, about 0.018 mg/kg, about 0.019 mg/kg, about 0.020 mg/kg, about 0.025 mg/kg, about 0.030 mg/kg and about 0.035 mg/kg body weight. In preferred embodiments, each dose of the selective dipeptidyl peptidase inhibitor (for example, FAP Inhibitor or DPP-8/DPP-9 inhibitor or DPP-8/DPP-9/FAP inhibitor) is administered at about 0.003 mg/kg, about 0.004 mg/kg, about 0.005 mg/kg, about 0.006 mg/kg, about 0.007 mg/kg, about 0.009 mg/kg, about 0.01 mg/kg, about 0.013 mg/kg and about 0.014 mg/kg.

In one embodiment, the present invention provides a method of treating a subject with prostate cancer by administering to the subject therapeutically effective amount of a selective dipeptidyl peptidase inhibitor and a PD-1 axis antagonist.

In one embodiment, the present invention provides a method of treating a subject with CrPC by administering to the subject therapeutically effective amount of a selective dipeptidyl peptidase inhibitor and a PD-1 axis antagonist.

In yet another embodiment, the present invention provides a method of treating a subject with abiraterone and/or enzalutamide resistant CrPC by administering to the subject a therapeutically effective amount of a selective dipeptidyl peptidase inhibitor and a PD-1 axis antagonist.

In yet another embodiment, the present invention provides a method of treating a subject with CrPC untreated with abiraterone and/or enzalutamide by administering to the subject a therapeutically effective amount of a selective dipeptidyl peptidase inhibitor with abiraterone and/or enzalutamide.

In one embodiment, abiraterone is administered at a dose from about 2 mg/kg to about 15 mg/kg, about 2 mg/kg to about 14 mg/kg, about 2 mg/kg to about 10 mg/kg, about 2 mg/kg to about 5 mg/kg, preferably about 3 mg/kg to about 4 mg/kg, more preferably about 3.5 mg/kg.

In one embodiment, enzalutamide is administered at a dose from about 0.5 mg/kg to about 2.8 mg/kg, about 1.2 mg/kg to about 2.8 mg/kg, preferably about 1.6 mg/kg to about 2.4 mg/kg, more preferably about 2.0 mg/kg to about 2.4 mg/kg.

XIII. Administration

Suitable administration/treatment protocols for treating prostate cancer or tumor in a subject include, for example, administering to the patient an effective amount of a selective dipeptidyl peptidase inhibitor (for example, talabostat or a pharmaceutically acceptable salt thereof) and a PD-1 axis antagonist.

In some embodiments, the combination therapy of the invention comprises administration of a selective dipeptidyl peptidase inhibitor (for example, talabostat or a pharmaceutically acceptable salt thereof) and a PD-1 axis antagonist. The selective dipeptidyl peptidase inhibitor and the PD-1 axis antagonist may be administered in any suitable manner known in the art. For example, the selective dipeptidyl peptidase inhibitor and the PD-1 axis antagonist may be administered sequentially (at different times) or concurrently (at the same time).

In some embodiments, the PD-1 axis antagonist and the selective dipeptidyl peptidase inhibitor is co-administered, for example, the administration of said PD-1 axis antagonist and the selective dipeptidyl peptidase inhibitor (for example talabostat or a pharmaceutically acceptable salt thereof) as two separate formulations. The co-administration can be simultaneous or sequential in either order or intermittently or continuously. In one further embodiment, there is a time period while both (or all) therapeutic agents simultaneously exert their biological activities. Said PD-1 axis antagonist and selective dipeptidyl peptidase inhibitor (for example talabostat or a pharmaceutically acceptable salt thereof) are co-administered either simultaneously or sequentially for example, oral or intravenous (i.v.) through a continuous infusion. When both therapeutic agents are co-administered sequentially the therapeutic agents are administered in two separate administrations that are separated by a "specific period of time". The term specific period of time is meant anywhere from 1 hour to 30 days. For example, one of the agents can be administered within about 30, 29, 28, 27, 26, 25, 24, 23, 22, 21, 20, 19, 18, 17, 16, 15, 14, 13, 12, 11, 10, 9, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour from the administration of the other therapeutic agent, and, in one embodiment, the specific period time is 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour. In some embodiments, simultaneous administration means at the same time or within a short period of time, usually less than 1 hour.

A dosing period as used herein is meant for a period of time, during which each therapeutic agent has been administered at least once. A dosing period is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, and, in one embodiment, 6, 7, 8, 9, 10, 11, 12, 13, 14, 16 or 24 days, for example, 8 or 16 or 24 days.

In certain embodiments, multiple (for example, 2, 3, 4, 5, 6, 7, 8, 9, 10 or more) doses of a selective dipeptidyl peptidase inhibitor (for example talabostat or a pharmaceutically acceptable salt thereof) and multiple (for example, 2, 3, 4, 5, 6, 7, 8, 9, 10 or more) doses of a PD-1 axis antagonist are administered to a subject in need of treatment.

In certain embodiments, the PD-1 axis antagonist is administered one dose per day, one dose every 2 days, one dose every 3 days, one dose every 4 days, one dose every 5 days, once a week, once every two weeks, once every three weeks or once every four weeks, preferably once a week. In certain embodiments, the PD-1 axis antagonist is administered as a single dose, in two doses, in three doses, in four doses, in five doses, or in 6 or more doses. The dosing schedule can vary from e.g., once a week to once every 2, 3, or 4 weeks. In one embodiment, the PD-1 axis antagonist is administered at a dose from about 1 mg/kg to 10 mg/kg once a week.

In certain embodiments, the selective dipeptidyl peptidase inhibitor is administered twice a day, one dose per day, one dose every 2 days, one dose every 3 days, one dose every 4 days, one dose every 5 days, once a week, once every two weeks, or once every four weeks, preferably one dose per day. In certain embodiments, the selective dipeptidyl peptidase inhibitor is administered as a single dose, in two doses, in three doses, in four doses, in five doses, or in 6 or more doses. The dosing schedule can vary from e.g., once a day to once every 2, 3, or 4 weeks. In one embodiment, the selective dipeptidyl peptidase inhibitor is administered at a dose from about 0.001 mg/kg to 3 mg/kg once a day. In certain embodiments the dose frequency may vary from twice a day to once very month.

Suitable treatment protocols for treating a human patient afflicted with cancer include, for example, administering to the patient an effective amount of each of:
(i) Talabostat or a pharmaceutically acceptable salt thereof,
(ii) a PD-1 axis antagonist
wherein the method comprises at least one administration cycle, wherein the cycle is a period of 24 days, wherein for each of the at least one cycles, talabostat or a pharmaceutically acceptable salt thereof administered continuously for seven days at a dose of about 0.001 mg/kg to 0.035 mg/kg body weight and the PD-1 axis antagonist is administered at a dose of 0.1-20 mg/kg body weight on every eighth day, after this 24 days cycle and a rest period of 7 days is recommended and then next administration cycle is started until there is relief in the disease state or as directed by the physician. This included the administration of PD-1 axis antagonist at a regular interval (for example, once a week) after the dosing of selective dipeptidyl peptidase inhibitor (for example, talabostat or a pharmaceutically acceptable salt thereof).

In another embodiment, the selective dipeptidyl peptidase inhibitor is formulated for oral administration and/or PD-1 axis antagonist is formulated for intravenous administration. In one embodiment, the PD-1 axis antagonist is administered on days 8, 16, 24 of each cycle. In another embodiment, the selective dipeptidyl peptidase inhibitor is administered daily. In the preferred embodiment, the administration cycle comprises once a day administration of talabostat or a pharmaceutically acceptable salt thereof on day 1, 2, 3, 4, 5, 6, 7, 9, 10, 11, 12, 13, 14, 15, 17, 18, 19, 20, 21, 22 and 23; and once a day administration of PD-1 axis antagonist on day 8, 16 and 24 and followed by a rest period of 1 week.

In another embodiment. 21 doses of the selective dipeptidyl peptidase inhibitor are administered in the 24-days' cycle. In another embodiment, 3 doses of the PD-1 axis antagonist are administered on every eighth day for 24-days' cycle.

In another embodiment, a cycle of administration is 24 days, which can be repeated, as necessary. In another embodiment, the treatment consists of up to 12 cycles.

In one embodiment, the talabostat or a pharmaceutically acceptable salt thereof and PD-1 axis antagonist are administered at the following doses:
a) about 0.002 mg/kg of talabostat or a pharmaceutically acceptable salt thereof and 2 mg/kg or 3 mg/kg or 1200 mg of PD-1 axis antagonist;
b) about 0.003 mg/kg of talabostat or a pharmaceutically acceptable salt thereof and 2 mg/kg or 3 mg/kg or 1200 mg of PD-1 axis antagonist;
c) about 0.004 mg/kg of talabostat or a pharmaceutically acceptable salt thereof and 2 mg/kg or 3 mg/kg or 1200 mg of PD-1 axis antagonist:
d) about 0.005 mg/kg of talabostat or a pharmaceutically acceptable salt thereof and 2 mg/kg or 3 mg/kg or 1200 mg of PD-1 axis antagonist;
e) about 0.006 mg/kg of talabostat or a pharmaceutically acceptable salt thereof and 2 mg/kg or 3 mg/kg or 1200 mg of PD-1 axis antagonist;
f) about 0.007 mg/kg of talabostat or a pharmaceutically acceptable salt thereof and 2 mg/kg or 3 mg/kg or 1200 mg of PD-1 axis antagonist;
g) about 0.008 mg/kg of talabostat or a pharmaceutically acceptable salt thereof and 2 mg/kg or 3 mg/kg or 1200 mg of PD-1 axis antagonist;
h) about 0.009 mg/kg of talabostat or a pharmaceutically acceptable salt thereof and 2 mg/kg or 3 mg/kg or 1200 mg of PD-1 axis antagonist;
i) about 0.010 mg/kg of talabostat or a pharmaceutically acceptable salt thereof and 2 mg/kg or 3 mg/kg or 1200 mg of PD-1 axis antagonist;
j) about 0.012 mg/kg of talabostat or a pharmaceutically acceptable salt thereof and 2 mg/kg or 3 mg/kg or 1200 mg of PD-1 axis antagonist;
k) about 0.013 mg/kg of talabostat or a pharmaceutically acceptable salt thereof and 2 mg/kg or 3 mg/kg or 1200 mg of PD-1 axis antagonist;
l) about 0.014 mg/kg of talabostat or a pharmaceutically acceptable salt thereof and 2 mg/kg or 3 mg/kg or 1200 mg of PD-1 axis antagonist.

Accordingly, in one embodiment, the dose of the selective dipeptidyl peptidase inhibitor and PD-1 axis antagonist is calculated as mg/kg body weight. However, in another embodiment, the dose of the selective dipeptidyl peptidase inhibitor and/or PD-1 axis antagonist is a flat fixed dose that is fixed irrespective of the weight of the patient.

The selective dipeptidyl peptidase inhibitor (for example, talabostat or a pharmaceutically acceptable salt thereof) and the PD-1 axis antagonist may be administered by the same route of administration or by different routes of administration. In some embodiments, the selective dipeptidyl peptidase inhibitor is administered orally, intravenously, intramuscularly, subcutaneously, topically, rectally, transdermally, intratracheally, vaginally, intraperitoneally, intraorbitally, by implantation, by inhalation, intrathecally, intraventricularly or intranasally. The preferred route of administration is oral. The selective dipeptidyl peptidase inhibitor can be administered to a subject by any route that delivers the inhibitor to the affected site, either directly or indirectly. Delivery may be local (e.g., mucosal) systemic. The selective dipeptidyl peptidase inhibitor is administered orally, and a PD-1 axis antagonist is administered by a non-oral route.

In some embodiments, the PD-1 axis antagonist (for example anti-PD-L1 antibody) is administered intravenously, intramuscularly, subcutaneously, topically, orally, transdermally, intraperitoneally, intraorbitally, by implantation, by inhalation, intrathecally, intraventricularly, or intranasally, preferably intravenously. In some embodiments, the anti-PD-L1 antibody is administered with a selective dipeptidyl peptidase inhibitor (for example, talabostat or a pharmaceutically acceptable salt thereof).

XIV. Kits, Probes and Primers

The present invention contemplates the use of kits, probes and/or primers that can be used to stratify patients between responders and non-responders. Such kits can include reagents that detect the quantitative presence of selective dipeptidyl peptidases consisting DPP-8, DPP-9 or FAP and programmed death ligand-1 (PDL-1) or CD274 (DNA or mRNA or protein). For example, the kit can include probes and/or primers that selectively hybridize to DPP-8/DPP-9/FAP and PD-L1 DNA or mRNA. The kit can further include reagents such as probes, primers and/or antibodies to detect the presence and quantity of DPP-8/DPP-9/FAP and programmed death ligand-1 (PDL-1) or CD274. A kit herein can furthermore include reagents useful for detecting the presence and/or quantity of any one or more of the following markers DPP-8/DPP-9/FAP and programmed death ligand-1 (PD-L1) or CD274.

XV. Specific Embodiments of the Present Invention

Embodiment 1. A computer implemented method for identifying a cancer patient segment in a dataset comprising:
(a) receiving a dataset of a biological sample from the cancer patient;
(b) determining/analyzing the amplification and/or expression level of the genes including selective dipeptidyl peptidases consisting of DPP-8, DPP-9 or FAP and programmed death ligand-1 (PDL-1) or CD274 in the dataset of the biological sample received from the cancer patient; and,
(c) identifying the cancer patient segment in the dataset, wherein the amplification and/or expression level of selective dipeptidyl peptidases consisting of DPP-8, DPP-9 or FAP and programmed death ligand-1 (PDL-1) or CD274 exceeds a predetermined threshold level.

Embodiment 2. The method according to embodiment 1, wherein the type of cancer is castration resistant prostate cancer (CrPC).

Embodiment 3. The method according to embodiment 2, wherein the castration resistant prostate cancer (CrPC) comprises small cell cancer, large cell cancer, neuroendocrine prostate cancer (NEPC) or castration resistant prostate cancer neuroendocrine (CrPC-NE) and castration resistant prostate cancer (CrPC) pre-treated with Abiraterone and/or Enzalutamide.

Embodiment 4. The method according to embodiment 1, wherein the determining the amplification and/or expression level of the genes comprises an amplification assay, a hybridization assay, an immunoassay, immunohistochemistry, a western blot, a northern blot, a probe-based quantitative amplification assay, a whole genomic sequencing, a whole proteomic sequencing, RNA sequencing, a polymerase chain reaction (PCR) and a quantitative real-time polymerase chain reaction (qRT-PCR).

Embodiment 5. The method according to embodiment 1, wherein the biological sample comprises tumour cells; tumor associated stromal cells; tumor associated fibroblasts; tumor associated macrophages; other immune related cells selected from tumour infiltrating lymphocytes including CD8+ T cells, MDSCs and Tregs; NK cells, circulating tumour DNA (ctDNA); circulating tumour cells and combination thereof.

Embodiment 6. A method for selecting a subject with castration resistant prostate cancer (CrPC) for a combination therapy comprising a selective dipeptidyl peptidase inhibitor and a PD-1 axis antagonist, said method comprising:
(a) obtaining a biological sample from the subject with castration resistant prostate cancer (CrPC);
(b) determining the amplification and/or expression level of the genes including selective dipeptidyl peptidases consisting of DPP-8, DPP-9 or FAP and programmed death ligand-1 (PD-L1) or CD274 in the biological sample obtained from the subject; and
(c) selecting the subject as a suitable candidate for the said therapy if based on an assessment that the amplification and/or expression level of selective dipeptidyl peptidases consisting of DPP-8, DPP-9 or FAP and programmed death ligand-1 (PDL-1) or CD274 exceeds a predetermined threshold level.

Embodiment 7. A method of treating a subject with a castration resistant prostate cancer (CrPC), said method comprising:
(a) selecting a subject according to method in embodiment 6; and
(b) administering to the subject a therapeutically effective amount of the selective dipeptidyl peptidase inhibitor and the PD-1 axis antagonist.

Embodiment 8. The method according to embodiment 6, wherein the determining the amplification and/or expression level of the genes comprises an amplification assay, a hybridization assay, an immunoassay, immunohistochemistry, a western blot, a northern blot, a whole genomic sequencing, a whole proteomic sequencing, RNA sequencing, a probe-based quantitative amplification assay, a polymerase chain reaction (PCR) and a quantitative real-time polymerase chain reaction (qRT-PCR).

Embodiment 9. The method according to embodiment 6, wherein the castration resistant prostate cancer (CrPC) comprises small cell cancer, large cell cancer, neuroendocrine prostate cancer (NEPC), castration-resistant prostate cancer-neuroendocrine (CrPC-NE) and castration resistant prostate cancer (CrPC) pre-treated with Abiraterone and/or Enzalutamide.

Embodiment 10. The method according to embodiment 6, wherein the biological sample comprises tumour cells; tumor associated stromal cells; tumor associated fibroblasts; tumor associated macrophages; other immune related cells selected from tumour infiltrating lymphocytes including CD8+ T cells, MDSCs and Tregs; NK cells, circulating tumour DNA (ctDNA); circulating tumour cells and combination thereof.

Embodiment 11. The method according to embodiment 6, wherein the subject is human.

Embodiment 12. The method according to embodiment 6, wherein the selective dipeptidyl peptidase inhibitor is talabostat or a pharmaceutically acceptable salt thereof.

Embodiment 13. The method according to embodiment 6, wherein the PD-1 axis antagonist consisting of PD-1 antagonist, PDL-1 antagonist and PDL-2 antagonist.

Embodiment 14. The method according to embodiment 13, wherein the PD-1 antagonist selected from the group consisting of ANA011, AUNP-12, BGB-A317, KD033, pembrolizumab, MCLA-134, mDX400, MEDI0680, muDX400, nivolumab, PDR001, PF-06801591, REGN-2810, SHR-1210, STI-A1110, TSR-042, ANB011 and XCE853 and combination thereof.

Embodiment 15. The method according to embodiment 13, wherein the PDL-1 antagonist selected from the group consisting of avelumab. BMS-936559, CA-170, durvalumab, MCLA-145, SP142, STI-A1011, STI-A1012, STI-A1010, STI-A1014 and atezolimumab and combination thereof.

Embodiment 16. The method according to embodiment 13, wherein the PDL-2 antagonist consisting of AMP-224 and rHIgM12B7 and combination thereof.

Embodiment 17. A method for determining likelihood that a therapy involving administration of a selective dipeptidyl peptidase inhibitor and a PD-1 axis antagonist to a subject afflicted with castration resistant prostate cancer (CrPC) provides a therapeutic benefit to the subject which comprises:
(a) determining the amplification and/or expression level of the genes including dipeptidyl peptidases consisting of DPP-8, DPP-9 or FAP and programmed death ligand-1 (PDL-1) or CD274 in a biological sample obtained from the subject who is receiving the said therapy;
(b) comparing the amplification and/or expression level of the genes including dipeptidyl peptidases consisting of DPP-8, DPP-9 or FAP and programmed death ligand-1 (PDL-1) or CD274 so obtained from the subject after receiving the said therapy to a predetermined threshold level of amplification and/or expression of respective genes in the biological sample of subjects who had a lack of therapeutic benefit from such a therapy; wherein, there is a likelihood that the therapy will provide the therapeutic benefit to the subject if the level of amplification and/or expression determined in step a) is less than the predetermined threshold level of expression.

Embodiment 18. The method according to embodiment 17, wherein the determining the amplification and/or expression level of the genes comprises an amplification assay, a hybridization assay, an immunoassay, immunohistochemistry, a western blot, a northern blot, a whole genomic sequencing, a whole proteomic sequencing, RNA sequencing, a probe-based quantitative amplification assay, a polymerase chain reaction (PCR) and a quantitative real-time polymerase chain reaction (qRT-PCR).

Embodiment 19. The method according to embodiment 17, wherein the castration resistant prostate cancer (CrPC) comprises small cell cancer, large cell cancer, neuroendocrine prostate cancer (NEPC), castration-resistant prostate cancer-neuroendocrine (CrPC-NE) and castration resistant prostate cancer (CrPC) pre-treated with Abiraterone and/or Enzalutamide.

Embodiment 20. The method according to embodiment 17, wherein the biological sample comprises tumour cells; tumor associated stromal cells; tumor associated fibroblasts; tumor associated macrophages; other immune related cells selected from tumour infiltrating lymphocytes including CD8+ T cells, MDSCs and Tregs; NK cells, circulating tumour DNA (ctDNA); circulating tumour cells and combination thereof.

Embodiment 21. The method according to embodiment 17, wherein the subject is human.

Embodiment 22. The method according to embodiment 17, wherein the selective dipeptidyl peptidase inhibitor is talabostat or a pharmaceutically acceptable salt thereof.

Embodiment 23. The method according to embodiment 17, wherein the PD-1 axis antagonist consisting of PD-1 antagonist, PDL-1 antagonist and PDL-2 antagonist.

Embodiment 24. The method according to embodiment 23, wherein the PD-1 antagonist selected from the group consisting of ANA011, AUNP-12, BGB-A317, KD033, pembrolizumab, MCLA-134, mDX400, MEDI0680, muDX400, nivolumab, PDR001, PF-06801591, REGN-2810, SHR-1210, STI-A1110, TSR-042, ANB011 and XCE853 and combination thereof.

Embodiment 25. The method according to embodiment 23, wherein the PDL-1 antagonist selected from the group consisting of avelumab, BMS-936559, CA-170, durvalumab, MCLA-145, SP142, STI-A1011, STI-A1012, STI-A1010, STI-A1014 and atezolimumab and combination thereof.

Embodiment 26. The method according to embodiment 23, wherein the PDL-2 antagonist consisting of AMP-224 and rHIgM12B7 and combination thereof.

Embodiment 27. A method of prognosing castration resistant prostate cancer (CrPC) in a subject; said method comprising: determining in a subject the amplification and/or expression level of the genes including selective dipeptidyl peptidases consisting of DPP-8, DPP-9 or FAP and programmed death ligand-1 (PD-1) or CD274 on a prognostic panel;
(a) comparing the determined amplification and/or expression level of the genes including selective dipeptidyl peptidases consisting of DPP-8, DPP-9 or FAP and programmed death ligand-1 (PDL-1) or CD274 to a predetermined threshold level; and
(b) prognosing a case of castration resistant prostate cancer (CrPC) if the determined amplification and/or expression level is higher than or exceeds the predetermined threshold level.

Embodiment 28. The method according to embodiment 27, wherein the determining the amplification and/or expression level of the genes comprises an amplification assay, a hybridization assay, an immunoassay, immunohistochemistry, a western blot, a northern blot, a whole genomic sequencing, a whole proteomic sequencing, RNA sequencing, a probe-based quantitative amplification assay, a polymerase chain reaction (PCR) and a quantitative real-time polymerase chain reaction (qRT-PCR).

Embodiment 29. The method according to embodiment 27, wherein the castration resistant prostate cancer (CrPC) comprises small cell cancer, large cell cancer, neuroendocrine prostate cancer (NEPC), castration-resistant prostate cancer-Neuroendocrine (CrPC-NE) and castration resistant prostate cancer (CrPC) pre-treated with Abiraterone and/or Enzalutamide.

Embodiment 30. The method according to embodiment 27, wherein the biological sample comprises tumour cells; tumor associated stromal cells; tumor associated fibroblasts; tumor associated macrophages; other immune related cells selected from tumour infiltrating lymphocytes including CD8+ Tcells, MDSCs and Tregs; NK cells, circulating tumour DNA (ctDNA); circulating tumour cells and combination thereof.

Embodiment 31. The method according to embodiment 27, wherein the subject is human.

Embodiment 32. The method according to embodiment 27, wherein the selective dipeptidyl peptidase inhibitor is alabostat or a pharmaceutically acceptable salt thereof.

Embodiment 33. The method according to embodiment 27, wherein the PD-1 axis antagonist consists of PD-1 antagonist, PDL-1 antagonist and PDL-2 antagonist.

Embodiment 34. The method according to embodiment 33, wherein the PD-1 antagonist selected from the group consisting of ANA011, AUNP-12, BGB-A317, KD033, pembrolizumab, MCLA-134, mDX400, MEDI0680, muDX400, nivolumab, PDR001, PF-06801591, REGN-2810, SHR-1210, STI-A1110, TSR-042, ANB011 and XCE853 and combination thereof.

Embodiment 35. The method according to embodiment 33, wherein the PDL-1 antagonist selected from the group consisting of avelumab, BMS-936559, CA-170, durvalumab, MCLA-145, SP142, STI-A1011, STI-A1012, STI-A1010, STI-A1014 and atezolimumab and combination thereof.

Embodiment 36. The method according to embodiment 33, wherein the PDL-2 antagonist consisting of AMP-224 and rHIgM12B7 and combination thereof.

Embodiment 37. A method for selecting a subject with prostate cancer for a combination therapy comprising a selective dipeptidyl peptidase inhibitor and a PD-1 axis antagonist, said method comprising:
(a) obtaining a biological sample from the subject with prostate cancer;
(b) determining the amplification and/or expression level of the genes including selective dipeptidyl peptidases consisting of DPP-8, DPP-9 or FAP and programmed death ligand-1 (PDL-1) or CD274 in the biological sample obtained from the subject; and
(c) selecting the subject as a suitable candidate for the said therapy if based on an assessment that the amplification and/or expression level of selective dipeptidyl peptidases consisting of DPP8. DPP-9 or FAP and programmed death ligand-1 (PDL-1) or CD274 exceeds a predetermined threshold level.

Embodiment 38. A method of treating prostate cancer, said method comprising:
(a) selecting a subject as per the method according to embodiment 37; and
(b) administering to the subject a therapeutically effective amount of the selective dipeptidyl peptidase inhibitor and the PD-1 axis antagonist.

Embodiment 39. The method according to embodiment 37, wherein the selective dipeptidyl peptidase inhibitor is talabostat or a pharmaceutically acceptable salt thereof and the PD-1 axis antagonist is pembrolizumab and nivolumab.

Embodiment 40. A method for selecting a subject with castration resistant prostate cancer (CrPC) untreated with abiraterone and/or enzalutamide for a combination therapy comprising a selective dipeptidyl peptidase inhibitor with abiraterone and/or enzalutamide:
(a) obtaining a biological sample from the subject with castration resistant prostate cancer (CrPC);
(b) determining the amplification and/or expression level of the genes including selective dipeptidyl peptidases consisting of DPP-8, DPP-9 or FAP; and
(c) selecting the subject as a suitable candidate for the said therapy if based on an assessment that the amplification and/or expression level of selective dipeptidyl peptidases consisting of DPP-8, DPP-9 or FAP exceeds a predetermined threshold level.

Embodiment 41. A method of treating castration resistant prostate cancer (CrPC) untreated with abiraterone and/or enzalutamide, said method comprising:
(a) selecting a subject as per the method according to embodiment 40; and
(b) administering to the subject a therapeutically effective amount of the selective dipeptidyl peptidase inhibitor with abiraterone and/or enzalutamide.

Embodiment 42. The method according to embodiment 41, wherein the selective dipeptidyl peptidase inhibitor is talabostat or a pharmaceutically acceptable salt thereof.

Embodiment 43. A method for predicting the response of a subject suffering from castration resistant prostate cancer (CrPC) to a combination therapy of selective dipeptidyl peptidase inhibitor and PD-1 axis antagonist, that comprises:
a) determining the amplification and/or expression level of the genes including selective dipeptidyl peptidase (DPP-8, DPP-9 or FAP) and programmed death ligand-1 (PDL-1) or CD274 in a biological sample from said subject;
b) comparing the amplification and/or expression level obtained in a) to a predetermined threshold value,
wherein, if the amplification and/or expression level of the genes including selective dipeptidyl peptidase (DPP-8, DPP-9 or FAP) and programmed death ligand-1 (PDL-1) or CD274 in a biological sample are decreased compared to the predetermined threshold value, indicate response to said combination therapy.

Embodiment 44. The method according to embodiment 43, wherein the determining the amplification and/or expression level of the genes comprises an amplification assay, a hybridization assay, an immunoassay, immunohistochemistry, a western blot, a northern blot, a whole genomic sequencing, a whole proteomic sequencing, RNA sequencing, a probe-based quantitative amplification assay, a polymerase chain reaction (PCR) and a quantitative real-time polymerase chain reaction (qRT-PCR).

Embodiment 45. The method according to embodiment 43, wherein the castration resistant prostate cancer (CrPC) comprises of small cell cancer, large cell cancer, neuroendocrine prostate cancer (NEPC), castration-resistant prostate cancer-Neuroendocrine (CrPC-NE) and castration resistant prostate cancer (CrPC) pre-treated with Abiraterone and/or Enzalutamide.

Embodiment 46. The method according to embodiment 43, wherein the biological sample comprises tumour cells; tumor associated stromal cells; tumor associated fibroblasts; tumor associated macrophages; other immune related cells selected from tumour infiltrating lymphocytes including CD8+ Tcells, MDSCs and Tregs; NK cells, circulating tumour DNA (ctDNA); circulating tumour cells and combination thereof.

Embodiment 47. The method according to embodiment 43, wherein the subject is human.

Embodiment 48. The method according to embodiment 43, wherein the selective dipeptidyl peptidase inhibitor is talabostat or a pharmaceutically acceptable salt thereof.

Embodiment 49. The method according to embodiment 43, wherein the PD-1 axis antagonist consisting of PD-1 antagonist, PDL-1 antagonist and PDL-2 antagonist.

Embodiment 50. The method according to embodiment 49, wherein the PD-1 antagonist selected from the group consisting of ANA011, AUNP-12, BGB-A317, KD033, pembrolizumab, MCLA-134, mDX400, MEDI0680, muDX400, nivolumab, PDR001, PF-06801591, REGN-2810, SHR-1210, STI-A1110, TSR-042, ANB011 and XCE853 and combination thereof.

Embodiment 51. The method according to embodiment 49, wherein the PDL-1 antagonist selected from the group consisting of avelumab, BMS-936559, CA-170, durvalumab, MCLA-145, SP142, STI-A1011, STI-A1012, STI-A1010, STI-A1014 and atezolimumab and combination thereof.

Embodiment 52. The method according to embodiment 49, wherein the PDL-2 antagonist consisting of AMP-224 and rHIgM12B7 and combination thereof.

XVI. Methods of Detection: Amplification and/or Expression Level of the DPP-8, DPP-9 or FAP and PDL-1 Genes are Detected Using the Following Methods (i) Chromosomal localization of DPP-8 and PDL-1 by Fluorescence in Situ Hybridization (FISH) analysis
(ii) Real time quantitative polymerase chain reaction (RT-QPCR) to measure the expression of DPP-8 and DPP-9
(iii) Immunohistochemistry (IHC)
(iv) Other methods like Northern blotting, Western blotting, whole exome sequencing, whole genome sequencing or RNA sequencing can also be used to detect amplification and/or expression level of genes DPP-8, DPP-9, FAP and PDL-1.

EXAMPLES

Example 1

Efficacy Study of Talabostat Mesylate and PD-1 Antagonist in Transgenic Mouse Model of NEPC (TRAMP Mouse)
Material and Methods:
Reagents and Antibodies: RPMI-1640 medium (Catalog No.: A1049101), Glutamax (Catalog No.: 35050061), Trypsin-EDTA (0.25%) (Catalog No.: 25200-056), Penicillin-Streptomycin (Catalog No.: 15070-063), HBSS (Catalog No.: 14175-095) are procured form Gibco, while Fetal bovine serum (FBS) (Catalog No.: 004-001-1A) is purchased from Biological Industries. The anti-PD-1 antibody (PD-1 antagonist (clone: RMPI-14, Catalog no: BE0146)) is supplied by Bioxcell at 6.61 mg/ml. Stock solutions of PD-1 antagonist, at 1 mg/ml concentrations are prepared and kept at 4° C. prior to use. Dosing solutions of PD-1 antagonist are prepared freshly at a concentration of 1 mg/ml, before every administration in sterile phosphate buffered saline (PBS), pH 7.0 and administered a dose of 10 mg/kg, intraperitoneally (i.p) into, 20 g mouse. The test article (talabostat mesylate) is acquired from a commercial source, and prepared freshly at a working concentration of 0.1 mg/ml before every administration in sterile phosphate buffered saline (pH 7.0), maintained at 4° C., and administered perorally (p.o) a total dose of 20 μg per 20 g mouse. Luminex panel for cytokine and chemokine analysis is used from Millipore.

Animals and tumor model: TRAMP (B16x129) mice (Greenberg N M, et al., Proc Natl Acad Sci USA, 92(8): 3439-3443) is backcrossed with FVB/N mice from the Jackson Laboratory for six generations. FVB/NTac mice are obtained from Taconic (Germantown, N.Y.). The treatments start when the mean tumor size reaches approximately 100-200 mm$^3$. The test article administration and the animal numbers in each study group are shown in the experimental design Table 1. The date of tumor cell inoculation is denoted as day 0. Animals are bred, housed and used in accordance to the Policy on Humane Care and Use of Laboratory Animals (Office of Laboratory Animal Welfare, National Institutes of Health, Bethesda, Md.).

The date of tumor cell inoculation is denoted as day 0. Six days post tumor implant, mice are sorted into groups of 12 mice with a mean tumor volume of ~140 mm$^3$ and the test article and antibody are administered according to the dosing schedules described in table 1, below:

TABLE 1

Treatment groups, dosing route and schedule

| Group | N | Treatment | Dose (mg/kg) | Dosing Route | Schedule |
|---|---|---|---|---|---|
| 1 | 12 | Talabostat mesylate | — | p.o. | QD |
|   |   | PD-1 antagonist |   | i.p. | Twice weekly × 3 weeks |
| 2 | 12 | Talabostat mesylate | 20 μg/dose | p.o. | QD |
| 3 | 12 | PD-1 antagonist | 10 | i.p. | Twice weekly × 3 weeks |
| 4 | 12 | Talabostat mesylate | 20 μg/dose | p.o. | QD |
|   |   | PD-1 antagonist | 10 | i.p. | Twice weekly × 3 weeks |

N: number of mice, QD: once daily, p.o.: per oral and i.p.: intraperitoneal.
Of the 12 mice in each group, three from each are sacrificed three days after the first dose of treatment is provided.

Tumor size and body weights are measured twice weekly. Tumor volumes are measured twice per week in two dimensions using a caliper, and the volume are expressed in mm$^3$ using the formula: V=0.5 a×b$^2$ where a and b are the length and width of the tumor, respectively. The entire procedures of dosing as well as tumor and body weight measurement are conducted in a Laminar Flow Cabinet. Tumor volume is expressed in mm$^3$, is measured with caliper on day 5, 8, 12, 15, 19, 22, 26 and day 29.

Expression of DPP-8, DPP-9, FAP and CD274: The tumor samples are analysed through microarray for the expression of DPP-8, DPP-9, FAP and CD274 before and after the therapy. q-RT-PCR and FACS are used for immune profiling to evaluate the efficacy of talabostat mesylate and the combination (talabostat mesylate and PD-1 antagonist) on expression of their target gene, as described below. While the blood samples as well as for the cytokine/chemokines are analysed by Luminex assay, as mentioned below. The vehicle control blood and tissue are also subjected to the same analysis in order the compare the efficacy of the talabostat mesylate and the combination with in terms of expression of the target genes and the cytokine and immune profile.

RNA Isolation: The tumors are stabilized in RNA Later (Life Technologies, Australia) and stored at −80° C. The tumors are disrupted in TRIzol (Life Technologies, Australia) employing a Tissue Ruptor rotor-stator homogenizer (QIAgen, Australia). After addition of chloroform and aqueous phase separation, the samples are purified on RNeasy MinElute columns (Qiagen, Australia). The integrity of the RNA samples is confirmed on the Bioanalyzer (Agilent Technologies, USA).

Microarrays: Total RNA samples of the 4 groups of 10 tumors/mice each are labeled and hybridized to Mouse Gene 1.0 ST microarrays (Affymetrix, USA). The microarray data is high quality; mean raw intensity of pm probes is measured; discrimination of positive versus negative control probes is also included where median absolute deviation of the residuals mean is considered relative to log expression mean.

DNA extraction, tumor purity, and exome sequencing: Slides are cut from frozen or fresh-frozen paraffin-embedded (FFPE) tissue blocks and examined by the study pathologists to select high-density cancer foci and ensure high purity of cancer DNA. All cases are also quantified for tumor purity using an algorithm called CLONET as described in Beltran et al. (2016, Nature Medicine, 22(3):298-305). The resultant tumor purity values are used to adjust the genomic data for downstream processing and analysis. Extraction and sequencing are performed using the extraction by Promega Maxwell 16 MDx, and stored at −20° C. Whole-exome capture libraries are constructed from tumor and normal tissue after sample-shearing, end repair, and phosphorylation and ligation to barcoded sequencing adaptors. Ligated DNA is size-selected for lengths between 200 and 350 bp and subjected to either exonic hybrid and captured using SureSelect v2/v4 Exome bait (Agilent) or HaloPlex Exome (Agilent) as described by Beltran et. al, (2016, Nature Medicine, 22(3):298-305). The samples are further subjected multiplexing and sequenced using Illumina HiSeq for an intended mean-target exome coverage of 100× for the tumor and germline samples.

Cytokine analysis of blood sample: For this the 100 μl blood is collected when randomized the mice, 3 days after first dosing as per the study. Blood samples are collected for obtaining serum and stored at −80° C. until analysis and the Luminex analysis is used for the detection of cytokines and the data is normalized.

Immunophenotyping of blood samples: The blood samples are collected from leg vein in anti-coagulant coated tubes. 5 μl of blood is mixed with staining buffer and respective antibodies, and stained on ice for 20 min, which is followed by RBC lysis. The RBC lysis reaction is terminated by adding PBS. The data are collected and analyzed on an ATTUNE Acoustic Nxt. The antibodies from BD Pharmingen for macrophages are used in this study. Samples are run (≥20,000 events) in duplicate on a BD LSRII flow cytometer using FACSDiva software (BD) for acquisition and compensation and analyzed using FlowJo software (FlowJo).

Immunophenotyping of tumor samples by RT-PCR: Tumor RNA samples are extracted from the frozen tumor tissues using the Trizol reagent. Reverse transcription is carried out using a kit from Takara (Catalog No. #RR047A). Quantitative PCR are conducted using a master mix from Invitrogen (Catalog No. #4309155) on an ABI 7900HT Fast Real-Time PCR System. The results are analyzed using a Delta Ct Method. The marker gene and respective oligo sequence used in this study are from the NIH q-RT-PCR primer database (mouseqprimerdepot.nih.gov) these are associated with the Ncrl and Pfrl (NK cell receptor) a marker characteristic to the NK cell and their activation respectively, while the Gmbz is meant for quantifying the release of granzyme B and the FoxP3 associated with CD25+CD4+ Tregs. Statistical Analysis: A one-way ANOVA is also used to assess the statistical difference between the vehicle group and all other groups in the blood sample immune-phenotyping and q-RT-PCR assay as well as on the microarray samples on the indicated day. All the data is analyzed using GraphPad Prism 5. $p<0.05$ is statistically significant (*, $p<0.05$; , $p<0.01$; *, $p<0.001$).

Result:

In the TRAMP mice the groups treated with talabostat mesylate 20 µg qd, in combination with PD-1 antagonist (10 mg/kg; twice weekly) exhibit significant tumor reduction as compared to PD-1 antagonist as well as vehicle control. While, talabostat mesylate alone showed a significant effect, the combination is resulted in complete regression of the tumor, confirming that talabostat mesylate substantially potentiates the effect of other immunotherapies.

As noted above, the inventors identified several genes or patterns in the cancer module that are involved in DPP-8, DPP-9 or FAP as well as CD274 overexpression and there is no androgen receptor (AR) expression found in TRAMP mouse before the combination therapy, while genes involved in neuroendocrinal characteristic that include Neuropeptide Y expression as well as synaptophysin are noted in the TRAMP mouse.

These data suggest that by pharmaceutically targeting several genes/hubs within the cancer module the inventors could indeed enhance the response rate to PD-1 antagonist. The inventors identified that the DPP-8/DPP-9/FAP are co-expressed with CD274, the gene for the ligand of PD-1 while after treatment with the said combination these reported genes show a decrease in their expression pattern as check by microarray. The robustness of this approach is exemplified by the gene expression associated with immune activation like IFN gamma, IL1 beta and TNF alpha as well as GM-CSF are upregulated in the TRAMP mice treated with talabostat mesylate and PD-1 antagonist, unlike that observed in the vehicle control groups. These data confirm that the target genes (selective dipeptidyl peptidases) of talabostat mesylate along with PDL-1 gene determine the response towards the drug.

A corroboration to the anti-tumor data is confirmed by the immunophenotyping of the tumor samples in the TRAMP mice. Moreover, the immunomodulation brought about by talabostat mesylate, shows a synergistic affect upon combination with PD-1 antagonist, as observed in the upregulation of pro-inflammatory cytokines including IL-2, IL-6, IL-12p40 as well as the profiles of chemokines that curtail the immunosuppressive microenvironment including GM-CSF and G-CSF.

It is further be noted that immunophenotyping of the minor samples on day 3 after the first dosing the revealed that the combination of talabostat mesylate with PD-1 antagonist increased the percentage of the cytotoxic NK cells and macrophages in the tumor while a decrease in the immunosuppressive T regulatory cells as compared the single agent and the vehicle control. The level of the mRNA transcript for the NK cell marker called natural cytotoxicity receptors are seen to be upregulated further in the animals administered with talabostat mesylate as well as PD-1 antagonist, as compared to the single agent treated groups. With respect to the macrophages which are of the tumoricidal phenotype as characterized with CD68 marker are seen to be synergistically enhanced in the tumors treated with the combination as compared to the single agent treated animals. The presence of this kind of macrophage population in the minor sample after the treatment therefore indicated that the combination of talabostat mesylate with PD-1 inhibitor promoted tumor infiltration of tumoricidal macrophages. Further, it is observed that in the tumor samples of the combination groups shows an appreciable decrease in the immunosuppresive Tregs.

The observation of reduction in the FoxP3 population in the tumor samples of groups treated by talabostat mesylate alone unlike that for the PD-1 antagonist treated group demonstrated the immune-upregulatory potential of talabostat mesylate. Thus, the combination of talabostat mesylate with PD-1 antagonist is able to induce a significant reduction in the FoxP3+ Treg population ($p<0.05$ as compared to PD-1 antagonist) as measured in terms of the relative mRNA expression of FoxP3.

Hence, it is inferred that the combining talabostat mesylate with PD-1 antagonist is able to bring about the anti-tumor effect through immune-modulation. The reduction in tumor volume as observed in the TRAMP mouse model of NEPC along with the reduction in the gene expression of the target genes and that of CD274 while an increase in the immune-stimulatory cytokines is noted and the combination showed an appreciable increase in the tumoricidal NK cells and CD68 macrophages while a significant decrease in the immune-suppressive Tregs.

Validation of the drug combinations for improving the response rate to immune checkpoint blockade in cancer, which can subsequently be taken to the clinic:

Further supporting the therapeutic potential of the combination between talabostat or a pharmaceutically acceptable salt thereof and immune-checkpoint inhibitor, an analysis of genomic alterations in FAP, DPP-8 and DPP-9 across a wide range of tumors singled out castration-resistant prostate cancer with a high level of DPP-9 amplification (14%). Further analysis revealed a very high correlation of PDL-1 amplification and overexpression along with the overexpression and amplification of the targets of talabostat, DPP-8 and DPP-9, in 50% of the patients which could make this patient population uniquely sensitive to the combination as shown by in-vitro and in-vivo experiments.

As proven in the in-silico experiments mentioned below:

Example 2

Evaluation of Talabostat Response Signature in Published Genomic Profiles of Tumors from 30 Different Organ Types For evaluation of talabostat response in different cancer types, amplification of DPP-8, DPP-9 and FAP (talabostat response signature) were queried in 39,525 copy number alteration (CNA) samples across 30 different organ types. The genomic profiles for CNA were queried on the web service interface of cBioPortal for cancer genomics version 1.10.2 [1,2]. Query was written in Onco Query Language (OQL) as 'FAP: AMP; DPP8: AMP; DPP9: AMP;' to identify cancer types which have highest amplification of the genes involved in talabostat response signature across the 39525 samples from 168 published studies. The details of the cancer studies have been shared in Table 2.1. (data source: http://www.cbioportal.org/data_sets.jsp)

Results: The amplification signature was mapped in 50 out of 168 studies with amplification alteration frequency ranging from 16.8% to 0.7%. The mapping of amplification signature across 168 cancer studies provided an opportunity to identify cancer types with higher likelihood of response to talabostat. The magnitude of alteration frequency was small for most of the cancer studies. Hence, with the threshold of amplification alteration frequency as 10% and minimum number of total cases in a cancer study as 100 cases, two cancer studies had positive amplification signature for talabostat response. The highest amplification alteration frequency of the response signature was observed 16.8% of 107 cases i.e. 18 cases in NEPC Study: Trento/Cornell/Broad 2015 (Beltran et al. Nat Med, 2016), followed by 11.01% of 109 i.e. 12 cases in Pancreas (UTSW) study (Table 2.2).

TABLE 2.1

Lists of public domain cancer genomic and transcriptomic studies with number of available samples per cancer study and data type for copy number alterations, or microarray as queried on cBioPortal version 1.10.2

| S. No. | Study Name | Reference | Institutional Affiliation | Total Samples in Study | CAN |
|---|---|---|---|---|---|
| 1 | Acinar Cell Carcinoma of the Pancreas | Jial et al. J Pathol 2014 | Johns Hopkins | 23 | 0 |
| 2 | Acute Myeloid Leukemia | TCGA, NEJM 2013 | TCGA | 200 | 191 |
| 3 | Acute Myeloid Leukemia | TCGA Provisional | TCGA | 200 | 191 |
| 4 | Adenoid Cystic Carcinoma | Ross et al. Am J Surg Pathl 2014 | FMI | 28 | 28 |
| 5 | Adenoid Cystic Carcinoma | Mitani et al. Clin Cancer Res 2015 | MDA | 102 | 0 |
| 6 | Adenoid Cystic Carcinoma | Ho et al. Nat Genet 2013 | MSKCC | 60 | 60 |
| 7 | Adenoid Cystic Carcinoma | Stephens et al. J Clin Invest 2013 | Sanger/ MDA | 24 | 0 |
| 8 | Adenoid Cystic Carcinoma of the Breast | Martelotto et al. J Pathol 2015 | MSKCC | 12 | 12 |
| 9 | Adrenocortical Carcinoma | TCGA Provisional | TCGA | 92 | 90 |
| 10 | Ampullary Carcinoma | Gingras et al. Cell Rep 2016 | Baylor College of Medicine | 160 | 0 |
| 11 | Bladder Cancer | Kim et al. Eur Urol 2015 | MSKCC | 109 | 109 |
| 12 | Bladder Cancer | Iyer et al. JCO 2013 | MSKCC | 97 | 97 |
| 13 | Bladder Cancer, Plasmacytoid Variant | Al-Ahmadie et al. Nat Genet 2016 | MSKCC | 34 | 33 |
| 14 | Bladder Urothelial Carcinoma | Guo et al. Nat Genet 2012 | BGI | 99 | 0 |
| 15 | Bladder Urothelial Carcinoma | Van Allen et al. Cancer Discov 2014 | Dana Farber & MSKCC | 50 | 0 |
| 16 | Bladder Urothelial Carcinoma | TCGA, Nature 2014 | TCGA | 131 | 128 |
| 17 | Bladder Urothelial Carcinoma | TCGA Provisional | TCGA | 413 | 408 |
| 18 | Brain Lower Grade Glioma | TCGA Provisional | TCGA | 530 | 513 |
| 19 | Breast Cancer | Pereira et al. Nat Commun 2016 | METABRIC | 2509 | 2173 |
| 20 | Breast cancer patient xenografts | Eirew et al. Nature 2014 | British Columbia | 117 | 30 |
| 21 | Breast Invasive Carcinoma | Shah et al. Nature | British Columbia | 65 | 0 |
| 22 | Breast Invasive Carcinoma | Banerji et al. Nature 2012 | Broad | 103 | 0 |
| 23 | Breast Invasive Carcinoma | Stephens et al. Nature 2012 | Sanger | 100 | 0 |
| 24 | Breast Invasive Carcinoma | TCGA, Cell 2015 | TCGA | 818 | 816 |
| 25 | Breast Invasive Carcinoma | TCGA, Nature 2012 | TCGA | 825 | 778 |
| 26 | Breast Invasive Carcinoma | TCGA Provisional | TCGA | 1105 | 1080 |

TABLE 2.1-continued

Lists of public domain cancer genomic and transcriptomic studies with number of available samples per cancer study and data type for copy number alterations, or microarray as queried on cBioPortal version 1.10.2

| S. No. | Study Name | Reference | Institutional Affiliation | Total Samples in Study | CAN |
|---|---|---|---|---|---|
| 27 | Cancer Cell Line Encyclopedia | Barretina et al. Nature 2012 | Novartis/ Broad | 1020 | 995 |
| 28 | Cervical Squamous Cell Carcinoma and Endocervical Adenocarcinoma | TCGA Provisional | TCGA Provisional | 309 | 295 |
| 29 | Cholangiocarcinoma | Chan-on et al. Nat Genet 2013 | National Cancer Centre of Singapore | 15 | 0 |
| 30 | Cholangiocarcinoma | Ong et al. Nat Genet 2012 | National University of Singapore | 8 | 0 |
| 31 | Cholangiocarcinoma | TCGA Provisional | TCGA Provisional | 36 | 36 |
| 32 | Chronic Lymphocytic Leukemia | Landau et al. Cell 2013 | Broad | 160 | 0 |
| 33 | Chronic Lymphocytic Leukemia | Puente et al. Nature 2015 | IUOPA | 506 | 0 |
| 34 | Clear Cell Renal Cell Carcinoma | Sato et al. Nat Genet 2013 | U Tokyo | 106 | 0 |
| 35 | Colorectal Adenocarcinoma | Giannakis et al. Cell Rep 2016 | DFCI | 619 | 0 |
| 36 | Colorectal Adenocarcinoma | Seshagiri et al. Nature 2012 | Genentech | 72 | 0 |
| 37 | Colorectal Adenocarcinoma | TCGA, Nature 2012 | TCGA | 276 | 257 |
| 38 | Colorectal Adenocarcinoma | TCGA Provisional | TCGA | 633 | 616 |
| 39 | Colorectal Adenocarcinoma Triplets | Brannon et al. Genome Biol 2014 | MSKCC | 138 | 0 |
| 40 | Cutaneous squamous cell carcinoma | Li et al, Clin Cancer Res 2015 | DFCI | 29 | 0 |
| 41 | Cutaneous T Cell Lymphoma | da Silva Almeida et al. Nat Genet 2015 | Columbia U | 42 | 0 |
| 42 | Cystic Tumor of the Pancreas | Wu et al. PNAS 2011 | Johns Hopkins | 32 | 0 |
| 43 | Desmoplastic Melanoma | Shain et al. Nat Genet 2015 | Broad Institute | 20 | 0 |
| 44 | Diffuse Large B-Cell Lymphoma | Lohr et al. PNAS 2012 | Broad | 58 | 0 |
| 45 | Esophageal Adenocarcinoma | Dulak et al. Nat Genet 2013 | Broad | 151 | 0 |
| 46 | Esophageal Carcinoma | TCGA Provisional | TCGA | 186 | 184 |
| 47 | Esophageal Squamous Cell Carcinoma | Song et al. Nature 2014 | ICGC | 88 | 0 |
| 48 | Esophageal Squamous Cell Carcinoma | Lin et al., Nat Genet 2014 | UCLA | 139 | 0 |
| 49 | Ewing Sarcoma | Tirode et al. Cancer Discov. 2014 | Institut Cuire | 249 | 0 |
| 50 | Gallbladder Carcinoma | Maolan Li et al, Nat Genet 2014 | Shanghai | 32 | 0 |
| 51 | Gastric Adenocarcinoma | Chen et al. PNAS 2015 | TMUCIH | 78 | 0 |
| 52 | Genetic Characterization of NSCLC young adult patients | Vaval̂ et al. Lung Cancer 2017 | University of Turin | 41 | 0 |
| 53 | Genomic Hallmarks of Prostate Adenocarcinoma | Fraser et al. Nature 2017 | CPC-GENE | 477 | 0 |
| 54 | Genomic Profile of Patients with Advanced Germ Cell Tumors | TCGA Provisional | MSK | 180 | 180 |
| 55 | Glioblastoma | TCGA, Cell 2013 | TCGA | 585 | 563 |
| 56 | Glioblastoma | TCGA, Nature 2008 | TCGA | 206 | 206 |
| 57 | Glioblastoma Multiforme | TCGA Provisional | TCGA | 604 | 577 |

TABLE 2.1-continued

Lists of public domain cancer genomic and transcriptomic studies with
number of available samples per cancer study and data type for copy number
alterations, or microarray as queried on cBioPortal version 1.10.2

| S. No. | Study Name | Reference | Institutional Affiliation | Total Samples in Study | CAN |
|---|---|---|---|---|---|
| 58 | Head and Neck Squamous Cell Carcinoma | Stransky et al. Science 2011 | Broad | 74 | 0 |
| 59 | Head and Neck Squamous Cell Carcinoma | Agrawal et al. Science 2011 | Johns Hopkins | 32 | 0 |
| 60 | Head and Neck Squamous Cell Carcinoma | TCGA, Nature 2015 | TCGA | 279 | 279 |
| 61 | Head and Neck Squamous Cell Carcinoma | TCGA Provisional | TCGA | 530 | 522 |
| 62 | Hepatocellular Adenoma | Pilati et al. Cancer Cell 2014 | Inserm | 46 | 0 |
| 63 | Hepatocellular Carcinomas | Schulze et al. Nat Genet 2015 | Inserm | 243 | 0 |
| 64 | Hypodiploid Acute Lymphoid Leukemia | Holmfeldt et al. Nat Genet 2013 | St Jude | 44 | 0 |
| 65 | Infant MLL-Rearranged Acute Lymphoblastic Leukemia | Andersson et al. Nat Genet 2015 | St Jude | 93 | 0 |
| 66 | Insulinoma | Cao et al. Nat Commun 2013 | Shanghai | 10 | 0 |
| 67 | Intrahepatic Cholangiocarcinoma | Jiao et al. Nat Genet 2013 | Johns Hopkins University | 40 | 0 |
| 68 | Kidney Chromophobe | TCGA, Cancer Cell 2014 | TCGA | 66 | 66 |
| 69 | Kidney Chromophobe | TCGA Provisional | TCGA | 66 | 66 |
| 70 | Kidney Renal Clear Cell Carcinoma | Guo et al. Nat Genet 2012 | BGI | 98 | 0 |
| 71 | Kidney Renal Clear Cell Carcinoma | TCGA, Nature 2013 | TCGA | 499 | 436 |
| 72 | Kidney Renal Clear Cell Carcinoma | TCGA Provisional | TCGA | 538 | 528 |
| 73 | Kidney Renal Papillary Cell Carcinoma | TCGA Provisional | TCGA | 293 | 288 |
| 74 | Liver Hepatocellular Carcinoma | Ahn et al. Hepatology 2014 | AMC | 231 | 231 |
| 75 | Liver Hepatocellular Carcinoma | Fujimoto et al. Nat Genet 2012 | RIKEN | 27 | 0 |
| 76 | Liver Hepatocellular Carcinoma | TCGA Provisional | TCGA | 442 | 370 |
| 77 | Low-Grade Gliomas | Johnson BE et al, Science 2014 | UCSF | 61 | 0 |
| 78 | Lung Adenocarcinoma | Imielinksi et al. Cell 2012 | Broad | 183 | 182 |
| 79 | Lung Adenocarcinoma | Rizvi et al., Science 2015 | MSKCC 2015 | 35 | 0 |
| 80 | Lung Adenocarcinoma | TCGA, Nature 2014 | TCGA | 230 | 230 |
| 81 | Lung Adenocarcinoma | TCGA Provisional | TCGA | 522 | 516 |
| 82 | Lung Adenocarcinoma | Ding et al. Nature 2008 | TSP | 163 | 0 |
| 83 | Lung Squamous Cell Carcinoma | TCGA, Nature 2012 | TCGA | 178 | 178 |
| 84 | Lung Squamous Cell Carcinoma | TCGA Provisional | TCGA | 504 | 501 |
| 85 | Lymphoid Neoplasm Diffuse Large B-cell Lymphoma | TCGA Provisional | TCGA | 48 | 48 |
| 86 | Malignant Peripheral Nerve Sheath Tumor | Lee et al. Nat Genet 2014 | MSKCC | 15 | 15 |
| 87 | Malignant Pleural Mesothelioma | Guo et al. Cancer Res 2015 | NYU | 22 | 0 |
| 88 | Mantle Cell Lymphoma | Bea et al. PNAS 2013 | IDIBIPS | 29 | 0 |
| 89 | Medulloblastoma | Pugh et al. Nature 2012 | Broad | 92 | 0 |
| 90 | Medulloblastoma | Jones et al. Nature 2012 | ICGC | 125 | 0 |
| 91 | Medulloblastoma | Robinson et al. Nature 2012 | PCGP | 37 | 0 |

TABLE 2.1-continued

Lists of public domain cancer genomic and transcriptomic studies with number of available samples per cancer study and data type for copy number alterations, or microarray as queried on cBioPortal version 1.10.2

| S. No. | Study Name | Reference | Institutional Affiliation | Total Samples in Study | CAN |
|---|---|---|---|---|---|
| 92 | Medulloblastoma | Morrissy et al. Nature 2016 | Sickkids | 46 | 0 |
| 93 | Melanoma | Berger et al. Nature 2012 | Broad/Dana Farber | 26 | 0 |
| 94 | Merged Cohort of LGG and GBM | TCGA, Cell 2016 | TCGA | 1122 | 1084 |
| 95 | Mesothelioma | TCGA Provisional | TCGA | 87 | 87 |
| 96 | Metastatic Prostate Cancer, SU2C/PCF Dream Team | Robinson et al. Cell. 2015 | Robinson et al. | 150 | 150 |
| 97 | MSK-IMPACT Clinical Sequencing Cohort | Zehir et al. Nat Med 2017 | MSKCC | 10945 | 10945 |
| 98 | MSK-IMPACT Clinical Sequencing Cohort for Non-Small Cell Cancer | Jordan E J et al. Cancer Discov 2017 | MSK | 915 | 915 |
| 99 | MSK-IMPACT Clinical Sequencing Cohort in Prostate Cancer | Abida et al, JCO Precision Oncology 2017 | MSK | 504 | 501 |
| 100 | Multiple Myeloma | Lohr et al. Cancer Cell 2014 | Broad | 211 | 0 |
| 101 | Multiregion Sequencing of Clear Cell Renal Cell Carcinoma | Gerlinger et al. Nat Genet 2014 | IRC | 79 | 0 |
| 102 | Mutational profiles of metastatic breast cancer | TCGA Provisional | France | 216 | 216 |
| 103 | Myelodysplasia | Yoshida et al. Nature 2011 | Tokyo | 29 | 0 |
| 104 | Nasopharyngeal Carcinoma | Lin et al., Nat Genet 2014 | Singapore | 56 | 0 |
| 105 | NCI-60 Cell Lines | Reinhold et al., Cancer Res. 2012 | NCI | 60 | 60 |
| 106 | Neuroblastoma | Molenaar et al. Nature 2012 | AMC Amsterdam | 87 | 0 |
| 107 | Neuroblastoma | Peifer et al. Nature 2015 | Broad | 56 | 0 |
| 108 | Neuroendocrine Prostate Cancer | Beltran et al. Nat Med 2016 | Trento/Cornell/Broad 2016 | 114 | 107 |
| 109 | Next generation sequencing | TCGA Provisional | NGS of pre-treatment metastatic melanoma samples | 66 | 66 |
| 110 | NGS in Anaplastic Oligodendroglioma and Anaplastic Oligoastrocytomas tumors | Thomas et al. Neuro Oncol 2017 | MSK | 22 | 22 |
| 111 | Oral Squamous Cell Carcinoma | Pickering et al. Cancer Discov 2013 | MD Anderson | 40 | 0 |
| 112 | Ovarian Serous Cystadenocarcinoma | TCGA, Nature 2011 | TCGA | 563 | 489 |
| 113 | Ovarian Serous Cystadenocarcinoma | TCGA Provisional | TCGA | 606 | 579 |
| 114 | Paired-exome sequencing of acral melanoma | Liang et al. Genome Res 2017 | TGEN | 38 | 38 |
| 115 | Pan-Lung Cancer | TCGA, Nat Genet 2016 | TCGA | 1144 | 1144 |
| 116 | Pancreatic Adenocarcinoma | Biankin et al. Nature 2012 | ICGC | 99 | 0 |
| 117 | Pancreatic Adenocarcinoma | Bailey et al. Nature 2016 | QCMG | 456 | 0 |
| 118 | Pancreatic Adenocarcinoma | TCGA Provisional | TCGA | 186 | 184 |
| 119 | Pancreatic Cancer | Witkiewicz et al. Nat Commun 2015 | UTSW | 109 | 109 |

TABLE 2.1-continued

Lists of public domain cancer genomic and transcriptomic studies with number of available samples per cancer study and data type for copy number alterations, or microarray as queried on cBioPortal version 1.10.2

| S. No. | Study Name | Reference | Institutional Affiliation | Total Samples in Study | CAN |
|---|---|---|---|---|---|
| 120 | Pancreatic Neuroendocrine Tumors | Jiao et al. Science 2011 | Johns Hopkins University | 10 | 0 |
| 121 | Papillary Thyroid Carcinoma | TCGA, Cell 2014 | TCGA | 507 | 496 |
| 122 | Pediatric Ewing Sarcoma | Brian D. Crompton et al. Cancer Discov 2014 | DFCI | 107 | 0 |
| 123 | Pheochromocytoma and Paraganglioma | TCGA Provisional | TCGA | 184 | 162 |
| 124 | Poorly-Differentiated and Anaplastic Thyroid Cancers | Landa et al. JCI 2016 | MSKCC | 117 | 117 |
| 125 | Primary Central Nervous System Lymphoma | Braggio E et al, Clin Cancer Res 2015 | Mayo Clinic | 19 | 0 |
| 126 | Prostate Adenocarcinoma | Baca et al. Cell 2013 | Broad/Cornell | 57 | 56 |
| 127 | Prostate Adenocarcinoma | Barbieri et al. Nat Genet 2012 | Broad/Cornell | 112 | 109 |
| 128 | Prostate Adenocarcinoma | Kumar et al. Nat Med 2016 | Fred Hutchinson CRC | 176 | 149 |
| 129 | Prostate Adenocarcinoma | Taylor et al. Cancer Cell 2010 | MSKCC | 216 | 194 |
| 130 | Prostate Adenocarcinoma | TCGA, Cell 2015 | TCGA | 333 | 333 |
| 131 | Prostate Adenocarcinoma | TCGA Provisional | TCGA | 499 | 492 |
| 132 | Prostate Adenocarcinoma CNA study | Hieronymus et al. PNAS 2014 | MSKCC | 104 | 104 |
| 133 | Prostate Adenocarcinoma Organoids | Gao et al., Cell 2014 | MSKCC | 12 | 0 |
| 134 | Prostate Adenocarcinoma, Metastatic | Grasso et al. Nature 2012 | Michigan | 61 | 61 |
| 135 | Recurrent and Metastatic Head & Neck Cancer | Morris et al. JAMA Oncol 2016 | MSKCC | 151 | 151 |
| 136 | Renal Non-Clear Cell Carcinoma | Durinck et al. Nat Genet 2014 | Genentech | 146 | 0 |
| 137 | Rhabdomyosarcoma | Shern et al. Cancer Discov 2014 | NIH | 43 | 0 |
| 138 | Sarcoma | Barretina et al. Nat Genet 2010 | MSKCC/Broad | 207 | 207 |
| 139 | Sarcoma | TCGA Provisional | TCGA | 265 | 257 |
| 140 | Skin Cutaneous Melanoma | Hodis et al. Cell 2012 | Broad | 121 | 0 |
| 141 | Skin Cutaneous Melanoma | TCGA Provisional | TCGA | 478 | 367 |
| 142 | Skm Cutaneous Melanoma | Krauthammer et al. Nat Genet 2012 | Yale | 91 | 0 |
| 143 | Small Cell Carcinoma of the Ovary | Jelinic et al. Nat Genet 2014 | MSKCC | 12 | 0 |
| 144 | Small Cell Lung Cancer | Peifer et al. Nat Genet 2012 | CLCGP | 29 | 0 |
| 145 | Small Cell Lung Cancer | Rudin et al. Nat Genet 2012 | Johns Hopkins | 51 | 0 |
| 146 | Small Cell Lung Cancer | George et al. Nature 2015 | U Cologne | 110 | 0 |
| 147 | Stomach Adenocarcinoma | Wang et al. Nat Genet 2014 | Pfizer and UHK | 100 | 0 |
| 148 | Stomach Adenocarcinoma | TCGA, Nature 2014 | TCGA | 295 | 293 |
| 149 | Stomach Adenocarcinoma | TCGA Provisional | TCGA | 478 | 441 |
| 150 | Stomach Adenocarcinoma | TCGA Provisional | U Tokyo | 30 | 0 |
| 151 | Stomach Adenocarcinoma | Wang et al. Nat Genet 2011 | UHK | 22 | 0 |

TABLE 2.1-continued

Lists of public domain cancer genomic and transcriptomic studies with number of available samples per cancer study and data type for copy number alterations, or microarray as queried on cBioPortal version 1.10.2

| S. No. | Study Name | Reference | Institutional Affiliation | Total Samples in Study | CAN |
|---|---|---|---|---|---|
| 152 | Targeted gene sequencing in 62 high-grade primary Unclassified Renal Cell Carcinoma | Chen et al. Nat Commun 2016 | MSK | 62 | 62 |
| 153 | Targeted sequencing of 1134 samples from metastatic colorectal cancer samples | TCGA Provisional | MSK | 1134 | 1134 |
| 154 | Targeted Sequencing of 341 samples from metastatic esophagogastric cancer patients | Janjigian et al. Cancer Discov 2017 | MSK, Cancer Discovery 2017 | 341 | 341 |
| 155 | TCGA data for Esophagus-Stomach Cancers | TCGA, Nature 2017 | TCGA | 559 | 288 |
| 156 | Testicular Germ Cell Cancer | TCGA Provisional | TCGA | 156 | 150 |
| 157 | The Metastatic Breast Cancer Project | TCGA Provisional | Provisional | 103 | 103 |
| 158 | Thymic Epithelial Tumors | Iacopo Petrini at el. Nat Genet 2014 | NCI | 32 | 0 |
| 159 | Thymoma | TCGA Provisional | TCGA | 124 | 123 |
| 160 | Thyroid Carcinoma | TCGA Provisional | TCGA | 516 | 499 |
| 161 | Uterine Carcinosarcoma | Jones et al. Nat Commun 2014 | Johns Hopkins University | 22 | 0 |
| 162 | Uterine Carcinosarcoma | TCGA Provisional | TCGA | 57 | 56 |
| 163 | Uterine Corpus Endometrial Carcinoma | TCGA, Nature 2013 | TCGA | 373 | 363 |
| 164 | Uterine Corpus Endometrial Carcinoma | TCGA Provisional | TCGA | 548 | 539 |
| 165 | Uveal Melanoma | TCGA Provisional | TCGA | 80 | 80 |
| 166 | Whole-exome sequences | TCGA Provisional | WES of pretreatment melanoma tumors | 39 | 0 |
| 167 | Whole-Genome Sequencing of Pancreatic Neuroendocrine Tumors | Scarpa et al. Nature 2017 | Nature | 98 | 0 |
| 168 | Whole-genome sequencing of pilocytic astrocytomasatic | Jones et al. Nat Genet 2013 | Nat Genetics | 96 | 0 |

TABLE 2.2

Studies with alteration frequency of response signature

| Study name | Reference | Total CNA cases | Number of cases for response signature amplified | Alteration frequency of response signature amplified |
|---|---|---|---|---|
| Neuroendocrine Prostate Cancer | Beltran et al. Nat Med 2016 | 107 | 18 | 16.8% |
| Pancreatic Cancer | Witkiewicz et al. Nat Commun 2015 | 109 | 12 | 11.01% |

Beltran et al, (Nature Medicine, Feb. 8, 2016, 22(3):298-305) further discloses CrPC-NE alterations could be detected earlier during CrPC adeno disease progression, for instance, then such individuals could potentially be selected for CrPC-NE-directed (such as platinum chemotherapy) rather than androgen receptor (AR)-targeted systemic therapies or for potentially co-targeting therapeutic approaches. Thus, there remains a high chance of the de-differentiation of an adenocarcinoma to a more progenitor-like cell state with some cells subsequently adopting neuroendocrine features due to local effects. The present inventors have analyzed the huge and undefined data sets provided in this article containing a data set for 107 patients with metastatic tumor and their normal tissue pair. The inventors, by applying computational analysis, surprising uncovered a very high correlation of programmed death ligand-1 (PDL-1) or CD274 amplification and overexpression along with the overexpression and amplification of the selective dipeptidyl peptidases (DPP-8/DPP-9/o FAP) which are the targets of talabostat, in 50% of the patients. This finding could make this patient population uniquely sensitive to the combination, of the selective dipeptidyl peptidase inhibitor and PD-1 axis antagonist. Thus, these data reveal the stage for dynamic testing of the reversibility of the CrPC-NE state with early intervention with selective dipeptidyl peptidase inhibitors and PD-1 axis antagonist.

Example 3

Identifying Patient Segment with the Talabostat Response Gene Signature in Combination with PDL-1 Target in the cBioPortal for Cancer Genomics Samples: With maximum alteration frequency for genes of talabostat or a pharmaceutically acceptable salt thereof response signature, 'Neuroendocrine Prostate Cancer (Trento/Cornell/Broad 2016)' study was interrogated for candidate genes of response signature along with PDL-1 (CD274). The patients in this study were clinically annotated as castration resistant prostate adenocarcinoma or castration resistant neuroendocrine prostate cancer. The samples were frozen or fresh frozen paraffin embedded (FFPE) tissue blocks and examined to ensure high purity of cancer DNA for cancer samples. For reference/normal germline (normal) DNA was obtained from either Peripheral Blood Mononuclear Cells (PBMCs) or benign tissue (number of subject: 81; samples: 114). Whole exome and RNASeq technologies were used to generate genomic and transcriptomic data respectively.

Genomic data for CNA: Whole exome sequencing used Illumina HiSeq for a mean target coverage of 100× for tumor and germline samples. Segmented data was used by CLONET to estimate purity and ploidy for each tumor. Each segment was represented by log2 of the ratio between values proportional to tumor and normal local coverage within genomic segment. Purified segment with mean log2 ratio less than −0.4 was reported as copy number loss and mean log2 ratio greater than 0.4 as copy number gain. Further, the data was processed via GISTIC (Genomic Identification of Segmented Targets) or RAE algorithm at cBioPortal to indicate the putative copy-number level per gene. Herein "−2" indicates a deep loss (possibly a homozygous deletion), "−1" indicates a shallow loss (possibly heterozygous deletion), "0" indicates diploid, "1" indicates a low-level gain, and "2" indicates a high-level amplification.

mRNA Expression data: For RNASeq, the frozen sample material was used to extract RNA and then prepared cDNA library. HiSeq 2500 was used to generate 2×75 by paired end reads. Further for data processing reads were mapped to the human genome reference sequence (hg19/GRC37), followed by quantification of gene level expression values as FPKM (fragments per kilobase of exon per million reads). FPKM values are estimated by counting all nucleotides mapped to each gene and were normalized by total number of mapped nucleotides (per million) and gene length (per kb). After transforming the FPKM via log2 (FPKM+1), the Mann-Whitney Wilcoxon test was performed for differential expression analysis. Finally, multiple hypotheses testing was performed using Benjamini Hochberg correction. As the data for this example was accessed from cBioPortal, threshold level for a gene is up- or down-regulated relative to the normal samples or all other tumor samples is Z-score with standard deviation of +2.0 (number of standard deviations away from the mean of expression in the reference population or EXP>=2 EXP<=−2). For mRNA expression data, relative expression of an individual gene in tumor sample are gene's expression distribution in a reference population wherein reference population refers to all that samples which are diploid for the gene in question (by default for mRNA), or normal samples (when specified), or all profiled samples.

Results: To assess the pattern of the candidate genes of response signature along with PDL-1, 'Neuroendocrine Prostate Cancer (Trento/Cornell/Broad 2016)' study from cBioPortal was analysed. This cancer study had highest alteration frequency of response signature as described in example 2. The response signature as amplification and/or expression level of one or more of the candidate genes of DPP-8, DPP-9, FAP along with CD274 (PDL-1) was observed in 45 patients in samples of both groups i.e. castration resistant prostate adenocarcinoma and castration resistant neuroendocrine prostate cancer. Additionally, these samples originated from tumor sites of different origin (Table 3, FIG. 1). The maximum Z-score observed for expression level for DPP-8 was 10.5, DPP-9 was 3.5 and for CD274 was 98.1. For CNA putative call for amplification level were positive for DPP-8 in 2 samples, DPP-9 in 15 samples, FAP in 4 samples and CD274 in 13 samples.

TABLE 3

Amplification status and mRNA expression level of 45 patients with positive response signature for amplification or overexpression of DPP-8, DPP-9 and FAP, along with CD274. cBioPortal version 1.10.2

| Patient ID | Sample ID | Amplification (presence/absence of positive amplification) | | | | Expression (z-score) | | | |
|---|---|---|---|---|---|---|---|---|---|
| | | DPP8 | DPP9 | FAP | CD274 | DPP8 | DPP9 | FAP | CD274 |
| WCMC159 | WCMC159_1_C | | | | | 0.815157 | −0.94206 | −1.24225 | 10.73756 |
| WCMC4240 | WCMC4240_1_N | ✓ | ✓ | | | 1.054021 | 3.533625 | −1.17912 | 17.24761 |
| WCMC119 | WCMC119_1_C | | ✓ | | ✓ | 1.067574 | 0.163037 | −1.22992 | 4.250123 |
| WCMC90 | WCMC90_3_C | | | | | 1.41857 | −0.47157 | −1.25009 | 10.68424 |
| WCMC210 | WCMC210_1_N | | ✓ | | ✓ | 1.473926 | −0.72308 | −1.2475 | 13.48222 |
| WCMC155 | WCMC155_1_N | | | | | 2.013332 | 1.873442 | −1.24426 | 14.94364 |
| WCMC9 | WCMC9_2_C | | | | | 2.102373 | −0.65723 | −1.1505 | 9.841974 |
| WCMC163 | WCMC163_1_N | | ✓ | | ✓ | 2.118078 | 0.06311 | −1.25398 | 10.32823 |
| WCMC90 | WCMC90_5_C | | | | | 2.1892 | −0.57759 | −1.2208 | 10.32325 |
| WCMC212 | WCMC212_1_N | | | | ✓ | 2.610845 | −0.90433 | −1.23845 | 2.145213 |
| WCMC192 | WCMC192_1_N | | ✓ | | | 2.77948 | −0.46579 | −0.86078 | 74.91695 |
| WCMC90 | WCMC90_1_C | | | | | 2.793726 | −0.8653 | −1.17216 | 23.14124 |
| WCMC159 | WCMC159_6_C | | | | | 2.823634 | −0.46726 | −1.18845 | 7.250899 |
| WCMC91 | WCMC91_1_C | | | | | 2.851705 | −0.89756 | −1.22796 | 8.106648 |
| WCMC90 | WCMC90_2_C | | | | | 2.921343 | −0.04712 | −1.13498 | 9.377424 |
| WCMC159 | WCMC159_2_C | | | | | 3.086398 | −0.39435 | −1.22614 | 13.39027 |
| WCMC2 | WCMC2_1_C | | | | | 3.227902 | 0.474249 | −1.18132 | 40.70436 |

TABLE 3-continued

Amplification status and mRNA expression level of 45 patients with positive response signature for amplification or overexpression of DPP-8, DPP-9 and FAP, along with CD274. cBioPortal version 1.10.2

| Patient ID | Sample ID | Amplification (presence/absence of positive amplification) | | | | Expression (z-score) | | | |
|---|---|---|---|---|---|---|---|---|---|
| | | DPP8 | DPP9 | FAP | CD274 | DPP8 | DPP9 | FAP | CD274 |
| WCMC14 | WCMC14_1_C | | | | ✓ | 3.283022 | −0.75035 | −1.22937 | 15.4232 |
| WCMC164 | WCMC164_1_C | | | | | 3.541144 | −0.97088 | −1.24224 | 28.5426 |
| WCMC169 | WCMC169_1_C | | | | | 3.61264 | 1.196995 | −0.35713 | 9.848795 |
| WCMC90 | WCMC90_4_C | | | | | 3.917847 | −0.37916 | −1.22193 | 4.417193 |
| WCMC159 | WCMC159_5_C | | | | | 4.057122 | −0.44182 | −1.21876 | 9.98042 |
| WCMC161 | WCMC161_1_C | | | | ✓ | 4.070793 | 0.087318 | −1.26208 | 34.08947 |
| WCMC139 | WCMC139_1_C | | | | | 4.32367 | −0.76894 | −1.2614 | 4.84119 |
| WCMC12 | WCMC12_2_N | | | | | 4.362098 | 2.423987 | −1.07636 | 16.02147 |
| WCMC162 | WCMC162_1_C | | | | | 4.375827 | 0.878921 | −0.68001 | 44.54207 |
| WCMC131 | WCMC131_1_C | | | | | 4.402518 | −0.34361 | −1.25477 | 11.53345 |
| WCMC172 | WCMC172_1_C | | | | | 5.261758 | −0.03555 | −1.25917 | 98.09211 |
| WCMC4 | WCMC4_1_C | | | | | 5.396945 | 2.288207 | −0.0552 | 39.51917 |
| WCMC159 | WCMC159_3_C | | | | | 5.408103 | −0.43397 | −1.22606 | 4.352875 |
| WCMC59 | WCMC59_1_C | | | | | 5.419954 | 0.502622 | −1.23962 | 8.24852 |
| WCMC187 | WCMC187_1_C | | | | | 5.456696 | 0.430629 | −1.16025 | 36.23213 |
| WCMC170 | WCMC170_1_C | | | | ✓ | 5.472426 | 0.984277 | −1.25918 | 22.75166 |
| WCMC9 | WCMC9_1_C | | | | | 5.552067 | 1.49124 | −1.25579 | 8.658128 |
| WCMC63 | WCMC63_1_C | | | | | 5.584165 | 0.372497 | −0.95179 | 7.344494 |
| WCMC195 | WCMC195_1_C | | | | ✓ | 5.763098 | 1.030651 | −1.1824 | 47.60006 |
| WCMC11 | WCMC11_1_C | | | | | 5.914922 | 0.838065 | −1.17814 | 45.65307 |
| WCMC188 | WCMC188_1_C | | | | ✓ | 6.117258 | 0.412883 | −1.23875 | 16.03106 |
| WCMC158 | WCMC158_1_C | | | | | 6.239236 | 0.317194 | −1.23975 | 21.65493 |
| WCMC89 | WCMC89_1_C | | | | | 6.366371 | 0.785655 | −1.19678 | 12.78989 |
| WCMC252 | WCMC252_1_N | | | | | 6.887182 | 1.161064 | −1.09907 | 10.65885 |
| WCMC0 | WCMC0_1_N | | | | | 8.049503 | 2.655043 | −1.22501 | 60.57061 |
| WCMC0 | WCMC0_8_N | | | | | 8.743902 | 2.495538 | −0.98067 | 50.30934 |
| WCMC189 | WCMC189_1_C | | | | | 9.11357 | 1.22452 | −1.23093 | 80.25742 |
| WCMC0 | WCMC0_10_N | | | | | 9.674249 | 2.586991 | −1.23661 | 47.37917 |
| WCMC0 | WCMC0_9_N | | | | | 10.15058 | 2.618514 | −1.1369 | 57.20084 |
| WCMC0 | WCMC0_5_N | | | | | 10.22031 | 2.598899 | −1.1993 | 78.98895 |
| WCMC0 | WCMC0_6_N | | | | | 10.50272 | 3.001589 | −1.19705 | 74.51467 |
| WCMC161 | WCMC161_2_N | | | | ✓ | NA | NA | NA | NA |
| WCMC161 | WCMC161_3_C | | | | ✓ | NA | NA | NA | NA |
| WCMC198 | WCMC198_1_N | | | | ✓ | NA | NA | NA | NA |
| WCMC6 | WCMC6_1_C | | ✓ | | ✓ | NA | NA | NA | NA |
| WCMC10364 | WCMC10364_1_N | ✓ | | ✓ | | NA | NA | NA | NA |
| WCMC121 | WCMC121_1_C | | | ✓ | | NA | NA | NA | NA |
| WCMC154 | WCMC154_1_N | | ✓ | | | NA | NA | NA | NA |
| WCMC183 | WCMC183_1_C | | ✓ | ✓ | | NA | NA | NA | NA |
| WCMC201 | WCMC201_1_C | | | ✓ | | NA | NA | NA | NA |
| WCMC207 | WCMC207_1_N | | ✓ | | | NA | NA | NA | NA |
| WCMC21016 | WCMC21016_2_C | | ✓ | | | NA | NA | NA | NA |
| WCMC243 | WCMC243_1_C | | ✓ | | | NA | NA | NA | NA |
| WCMC7520 | WCMC7520_2_N | | ✓ | | | NA | NA | NA | NA |
| WCMC7520 | WCMC7520_3_N | | ✓ | | | NA | NA | NA | NA |

Data Source: Neuroendocrine Prostate Cancer (Trento/Cornell/Broad 2016) study from cBioPortal version 1.10.2

Example 4

Mutual Exclusivity and Co-Occurrence Analysis for Candidate Genes (DPP-8, DPP-9 or FAP) of Response Signature Along with PDL-1

Mutual exclusivity and co-occurrence of genomic alterations in each of the three candidate genes (DPP-8, DPP-9 or FAP) of response signature along with the incidence of CD274 (PDL-1) alterations in 'Neuroendocrine Prostate Cancer (Trento/Cornell/Broad 2016)' study was evaluated using the cBioPortal for Cancer Genomics. This analysis was based on Mutual Exclusivity Modules for oncology datasets (Ciriello, et al., Genome Research, February 2012, 22(2):398-406). Here, for each gene combination "switching permutation" was implemented to calculate a p-value by fisher exact test and log odds ratio quantified the strength of association of alterations in gene A with an alteration found in gene B. The positive value of log-odds ratio suggests the co-occurrence of alterations in these genes in the same samples while negative value suggest that alterations in these genes are mutually exclusive and occur in different samples.

Results: All pairwise combination of query genes analysed for co-occurrence for cBioPortal of cancer genomics (Table 4). From all the six combinations of the candidate genes, we observed that there is a strong statistical tendency towards co-occurrence for CD274 with DPP-9 at log odds ratio of 1.2 and CD274 with DPP-8 at log odds ratio of 5.68. This suggests the possibility of higher likelihood of response, for therapeutic potential of talabostat in combination with PD-1 antagonist, in castration resistant prostate cancer patient segment.

TABLE 4

Results of co-occurrence analysis of alterations in talabostat response signature genes along with alterations of CD274 (PDL-1) in 'Neuroendocrine Prostate Cancer (Trento/Cornell/Broad 2016)' study from cBioPortal of cancer genomics. (where significant combinations are with p-value < 0.05 and are highlighted as bold)

| S. No. | Gene A | Gene B | Log Odds Ratio | p-Value | Association |
|---|---|---|---|---|---|
| 1 | CD274 | DPP9 | 1.204744707 | 0.011989 | Co-occurrence (Significant) |
| 9 | CD274 | DPP8 | 5.681309619 | 2.18E-21 | Co-occurrence (Significant) |

Literary and clinical evidence point out the atypical feature of prostate cancer as observed by the absence of a proportional increase in serum prostate-specific antigen level, bulky symptomatic tumor masses, exclusive visceral metastases, or a predominance of lytic bone metastases, is an indication of an aggressive prostate cancer variant. The characteristic feature of such aggressive variants of prostate cancer distinguishes neuroendocrine or small-cell carcinomas from the, which frequently lack androgen receptor expression and respond poorly to hormonal therapies.

This present study provides evidence for the differential expression data for the DPP-8 and DPP-9 and its association with the PDL-1 gene expression with respect to prostate cancer and in particular the differential expression pattern neuroendocrinal variant of the same. This finding therefore enable to categorize patient's therapeutic regime of the selective dipeptidyl peptidase inhibitor in combination with the PD-1 antagonist.

Example 5

The following is done on the clinical samples to confirm the findings for response of talabostat mesylate in combination with PD-1 antagonist:

A. Immunohistochemistry (IHC):

Human NEPC and/or mouse tumors are embedded in OCT (Optimum cutting temperature) compound (Tissue-Tek) and frozen at −80° C. before sectioning onto positively charged slides. Frozen human prostate tumor slides are prepared as described in Beltran et al., Cancer Discov. 2011 November; 1(6):487-95. Briefly slides are air dried for 20 min, and then fixed with cold acetone for 10 min at 4° C. Sections are then air dried (20 min), ished with phosphate buffered saline (PBS) (three times), and incubated with 0.3% hydrogen peroxide for 10 min to block endogenous peroxidase. After PBS ish (two times sections are blocked with protein block solution (Dako), ished with PBS (two times), and then further blocked with biotin/avidin block reagent (Invitrogen). After PBS ish (three times), sections are incubated with primary antibody or isotype control antibody for 45 min at room temperature in a humidified chamber. For human tissues, the FAP-specific antibody FAP5 (Ostermann et al., Clinical cancer research, Jul. 15, 2008 , 14(14):4584-4592) or mouse IgG2a isotype control antibody (BioLegend) are used at 0.625 µg/ml, and developed with the mouse Dako EnVision+ System-HRP (DAB) kit as recommended. FAP is detected in immersion fixed paraffin-embedded sections of human squamous cell carcinoma using sheep anti-human fibroblast activation protein alpha/FAP antigen affinity-purified polyclonal antibody (Catalog No. #AF3715) at 15 µg/mL overnight at 4° C. Tissue is stained using the anti-sheep HRP-DAB cell and tissue staining kit (brown; Catalog No. #CTS019) and counter stained with hematoxylin (blue). Specific staining is localized to connective tissue. For mouse tissues, FAP5 or mouse IgG2a isotype control antibodies are biotinylated (EZ-Link NHS PEG4-biotin; Thermo Fisher Scientific) and used at 2 µg/ml. Sections are developed with ABC reagent (Vector Laboratories) and DAB substrate (Dako). All slides are counterstained with hematoxylin, ished, dehydrated through graded alcohol and xylene, and then mounted. Stained human tissue sections are evaluated by a pathologist for: % stroma (of tumor section), % stromal cells positive for FAP (either >50% or <50%), and FAP staining intensity (0=no staining, 3+=strong staining). Further for the detection of PDL-1 and DPP-8 and DPP-9 in the human tissues the following antibodies and dilutions are used: anti-PDL-1 (rabbit polyclonal, Novis Biologicals, NBP1-76769), anti-DPP-8-catalytic domain (Ab42077as well as Ab42076, Abcam Inc, dilution 1:2000), anti-DPP-9-catalytic domain (Ab42089, Abcam Inc, dilution 1:2000) per Chowdhury S etal., World J Gastroenterol. May, 21, 2013 ; 19(19): 2883-2893 and Beltran. H. et al., Feb. 8, 2016; Nature medicine, 22(3):298-305. Also, as controls anti-synaptophysin (RM-9111-S, clone SP11, Thermo Scientific; dilution 1:100), anti-chromogranin A (MU126-UC, clone LK2H10, BioGenex, Calif., USA; dilution 1:400) is used and to determine positive expression a >20% of cells for synaptophysin and chromogranin A used as the cut-off.

B. Chromosomal Localization of DPP-8 and PDL-1 by Fluorescence in Situ Hybridization (FISH) Analysis:

DPP-8 is localized using two different probes, the DPP-8 EST (ESTAA417787) and the T8 clone as per the details available in the patent US20040191826 A1, while PDL-1 is detected using CD274 (PDL-1)/CEN9q FISH Probe as available from Abnova (Cat no. FG0160). The probes are nick-translated with biotin-C14-dATP and hybridized in situ at a final concentration of 10 ng/µl to metaphases from two normal males. The FISH method is modified from that previously described by McCaughan, G. W. etal., J. Gastroenterol. Hepatol., 1993, 8(2), 142-145. Briefly, the chromosomes are stained before analysis with both propidium iodide (as counterstain) and DAPI (for chromosomal identification). Images of metaphase preparations are captured by a cooled CCD camera using the Cyto Vision Ultra image collection and enhancement system (Applied Imaging International Ltd). FISH signals and the DAPI banding pattern are merged for figure preparation.

C. Real Time Quantitative Polymerase Chain Reaction to Measure the Expression of DPP-8 and DPP-9:

RNA from cells is extracted as described by Chowdhury S. et al (World J Gastroenterol. May 21, 2013; 19(19): 2883-2893.). Briefly, using the RNAqueous-Micro™ kit (Ambion, Tex., United States) following manufacturer's instructions. Total RNA (1 µg) is then reverse-transcribed to cDNA using 10 pmol of oligo(dT)12-18 primer (Invitrogen, Carlsbad, Calif., United States), 10 mmol/L deoxyribonucleotide triphosphates and SuperScript III reverse transcriptase (Invitrogen). Real time quantitative polymerase chain reaction (PCR) by Taqman® gene expression assays is performed using the Stratagene® Mx3000P™ System (La Jolla, Calif., United States) according to manufacturer's recommendations. Taqman primers used for the assays are mouse DPP-8 (Mm00547049_mL) and DPP-9 (Mm00841122_mL). The samples are run in duplicates. The gene expression level is analyzed using a standard curve of serially diluted known numbers of molecules of the same gene and then normalized relative to 18S (Hs99999901_s1). Quantitative PCR on human samples are performed using sequence detector (Prism, model 7700; Life Technologies, NY, United States) and are analyzed using sequence detector software (Prism, Version. 1.6.3; Applied Biosystems Inc.). Primers used for human DPP8 are forward: 5' CCA-GATGGACCTCATTCAGACAG-3' and reverse: 5'GGTTG TTGCGTAAATCCTTGTGG-3' and for human DPP9 are forward: 5'AGAAGCACCCCACCGTCCTCTTTG-3' and reverse: 5'AGGACCAGCCATGGATGGCAACTC-3'. While for PDL1 the forward and reverse primers are 5'-TATGGTGGTGCCGACTACAA-3', and 5'-TGGCTCCCAGAATTACCAAG-3' are used respectively (Metabion, Martinsried, Germany) as per Samuel T. Haile S. T. etal., described in J Immunol. Jun. 15, 2011; 186(12): 6822-6829. The number of molecules is normalized with human aldolase B (forward: 5'-CCTCGCTATCCAG-GAAAAC-3' and reverse: 5'TTGTAGACAGCAGC CAGGAC-3').

The tumor sample which show overexpression and amplification of DPP-8/DPP-9/FAP along with CD274 corresponds to the segment of patients from CrPC eligible for being treated with the combination of the selective dipeptidyl peptidase inhibitor and the PD-1 antagonist.

---

The invention claimed is:

1. A method for identifying an eligible prostate cancer patient to receive treatment for castration resistant prostate adenocarcinoma or castration resistant neuroendocrine prostate cancer, the method comprising:
   (a) obtaining a biological sample or a data set of biological samples from a prostate cancer patient;
   (b) determining an amplification and/or an expression level of one or more genes selected from the group consisting of DPP-8, DPP-9, FAP, and programmed death ligand-1 (PDL-1) or CD274 in the biological sample obtained from the prostate cancer patient; and,
   (c) identifying the prostate cancer patient as the eligible prostate cancer patient if the amplification and/or the expression level of DPP-8, DPP-9, FAP, and programmed death ligand-1 (PDL-1) or CD274, exceeds a predetermined threshold level;
   wherein the eligible prostate cancer patient is treated with a therapeutically effective amount of (i) talabostat or a pharmaceutically acceptable salt thereof, and (ii) a PD-1 axis antagonist.

2. The method of claim 1, wherein the eligible prostate cancer patient has castration resistant prostate cancer (CrPC).

3. The method of claim 1, wherein the amplification and/or expression level of the genes is determined by an amplification assay, a hybridization assay, an immunoassay, immunohistochemistry, a western blot, a northern blot, a probe-based quantitative amplification assay, a whole genomic sequencing, a whole proteomic sequencing, RNA sequencing, a polymerase chain reaction (PCR) or a quantitative real-time polymerase chain reaction (qRT-PCR).

4. The method of claim 1, wherein the biological sample comprises tumor cells; tumor associated stromal cells; tumor associated fibroblasts; tumor associated macrophages; other immune related cells selected from tumor infiltrating lymphocytes including CD8+ T cells, MDSCs and Tregs; NK cells, circulating tumor DNA (ctDNA); circulating tumor cells or combination thereof.

5. A method for treating a subject with castration resistant prostate adenocarcinoma or castration-resistant neuroendocrine prostate cancer wherein the treatment comprises a combination therapy comprising administering talabostat or a pharmaceutically acceptable salt thereof; and a PD-1 axis antagonist, said method comprising:
   (a) obtaining a biological sample from a subject with castration resistant prostate cancer (CrPC);
   (b) determining the amplification and/or expression level of one or more genes selected from the group consisting of DPP-8, DPP-9, FAP, and programmed death ligand-1 (PDL-1) or CD274 in the biological sample obtained from the subject;
   (c) selecting the subject as a suitable candidate for said treatment if based on an assessment that the amplification and/or expression level of the DPP-8, DPP-9, FAP, and programmed death ligand-1 (PDL-1) or CD274 exceeds a predetermined threshold level; and
   (d) administering to the subject a therapeutically effective amount of (i) talabostat or a pharmaceutically acceptable salt thereof; and (ii) PD-1 axis antagonist.

6. The method of claim 5, wherein the determining the amplification and/or expression level of the genes is determined by an amplification assay, a hybridization assay, an immunoassay, immunohistochemistry, a western blot, a northern blot, a whole genomic sequencing, a whole proteomic sequencing, RNA sequencing, a probe-based quantitative amplification assay, a polymerase chain reaction (PCR) or a quantitative real-time polymerase chain reaction (qRT-PCR).

7. The method of claim 5, wherein the biological sample comprises tumor cells; tumor associated stromal cells; tumor associated fibroblasts, tumor associated macrophages; other immune related cells selected from tumor infiltrating lymphocytes including CD8+T cells, MDSCs and Tregs; NK cells, circulating tumor DNA (ctDNA);
circulating tumor cells or combination thereof.

8. The method of claim 5, wherein the subject is human.

9. The method of claim 5, wherein the PD-1 axis antagonist is selected from the group consisting of PD-1 antagonist, PDL-1 antagonist, and PDL-2 antagonist.

10. The method of claim 9, wherein the PD-1 antagonist is selected from the group consisting of ANA011, AUNP-12, BGB-A317, KD033, pembrolizumab, MCLA-134, mDX400, MEDI0680, muDX400, nivolumab, PDR001, PF-06801591,REGN-2810, SHR-1210, STI-A1 110, TSR-042, and XCE853 and combinations thereof.

11. The method of claim 9, wherein the PDL-1 antagonist is selected from the group consisting of avelumab, BMS-936559, CA-170, durvalumab, MCLA-145, SP142, STI-A1011, STI- A1012, STI-AIOIO, STI-A1014 and atezolizumab and combinations thereof.

12. The method of claim 9, wherein the PDL-2 antagonist is selected from the group consisting of AMP-224 and rHIgM12B7 and combination thereof.

13. A method for treating a subject having castration-resistant prostate cancer adenocarcinoma or castration resistant neuroendocrine prostate cancer comprising: administering to the subject a therapeutically effective amount of (i) talabostat or a pharmaceutically acceptable salt thereof; and (ii) PD-1 axis antagonist.

14. The method of claim 13, wherein the subject is human.

15. The method of claim 13, wherein the PD-1 axis antagonist is selected from the group consisting of PD-1 antagonist, PDL-1 antagonist and PDL-2 antagonist.

16. The method of claim 15, wherein the PD-1 antagonist is selected from the group consisting of ANA011, AUNP-12, BGB-A317, KD033, pembrolizumab, MCLA-134, mDX400, MED10680, muDX400, nivolumab, PDR001, PF-06801591, REGN-2810, SHR-1210, STI-Al 110, TSR-042, and XCE853 and combinations thereof.

17. The method of claim 15, wherein the PDL-1 antagonist is selected from the group consisting of avelumab, BMS-936559, CA-170, durvalumab, MCLA-145, SP142, STI-A1011, STI-A1012, STI-A1010, STI-A1014 and atezolizumab and combinations thereof.

18. The method of claim 15, wherein the PDL-2 antagonist is selected from the group consisting of AMP-224 and rHIgM12B7 and combinations thereof.

19. The method of claim 15, wherein the PD-1 axis antagonist is a PD-1 antagonist.

20. The method of claim 16, wherein the PD-1 antagonist is pembrolizumab.

21. The method of claim 16, wherein the PD-1 antagonist is nivolumab.

* * * * *

SEQUENCE LISTING

```
<160> NUMBER OF SEQ ID NOS: 5

<210> SEQ ID NO 1
<211> LENGTH: 100
<212> TYPE: PRT
<213> ORGANISM: Artificial Sequence
<220> FEATURE:
<223> OTHER INFORMATION: Synthetic Peptide of Mouse monoclonal FAP
      antibody

<400> SEQUENCE: 1

Pro Pro Gln Phe Asp Arg Ser Lys Lys Tyr Pro Leu Leu Ile Gln Val
1               5                   10                  15

Tyr Gly Gly Pro Cys Ser Gln Ser Val Arg Ser Val Phe Ala Val Asn
            20                  25                  30

Trp Ile Ser Tyr Leu Ala Ser Lys Glu Gly Met Val Ile Ala Leu Val
        35                  40                  45

Asp Gly Arg Gly Thr Ala Phe Gln Gly Asp Lys Leu Leu Tyr Ala Val
    50                  55                  60

Tyr Arg Lys Leu Gly Val Tyr Glu Val Glu Asp Gln Ile Thr Ala Val
65                  70                  75                  80

Arg Lys Phe Ile Glu Met Gly Phe Ile Asp Glu Lys Arg Ile Ala Ile
                85                  90                  95

Trp Gly Trp Ser
            100

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide of  N-terminus of human FAP
      aa 57-73

<400> SEQUENCE: 2

Phe Phe Pro Asn Trp Ile Ser Gly Gln Glu Tyr Leu His Gln Ser Ala
1               5                   10                  15

Asp

<210> SEQ ID NO 3
<211> LENGTH: 50
<212> TYPE: PRT
<213> ORGANISM: Artificial Sequence
<220> FEATURE:
<223> OTHER INFORMATION: Synthetic peptide of C-terminal region of
      Human FAP

<400> SEQUENCE: 3

Ser Trp Glu Tyr Tyr Ala Ser Val Tyr Thr Glu Arg Phe Met Gly Leu
1               5                   10                  15

Pro Thr Lys Asp Asp Asn Leu Glu His Tyr Lys Asn Ser Thr Val Met
```

```
                    20                  25                  30

Ala Arg Ala Glu Tyr Phe Arg Asn Val Asp Tyr Leu Leu Ile His Gly
        35                  40                  45

Thr Ala
    50

<210> SEQ ID NO 4
<211> LENGTH: 77
<212> TYPE: PRT
<213> ORGANISM: Artificial Sequence
<220> FEATURE:
<223> OTHER INFORMATION: Synthetic peptide of C-terminal region of
      Human FAP

<400> SEQUENCE: 4

Glu Arg Cys Gln Tyr Tyr Thr Ala Ser Phe Ser Asp Tyr Ala Lys Tyr
1               5                   10                  15

Tyr Ala Leu Val Cys Tyr Gly Pro Gly Ile Pro Ile Ser Thr Leu His
            20                  25                  30

Asp Gly Arg Thr Asp Gln Glu Ile Lys Ile Leu Glu Glu Asn Lys Glu
        35                  40                  45

Leu Glu Asn Ala Leu Lys Asn Ile Gln Leu Pro Lys Glu Glu Ile Lys
    50                  55                  60

Lys Leu Glu Val Asp Glu Ile Thr Leu Trp Tyr Lys Met
65                  70                  75

<210> SEQ ID NO 5
<211> LENGTH: 288
<212> TYPE: PRT
<213> ORGANISM: Homo sapiens

<400> SEQUENCE: 5

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
```

```
            195                 200                 205
Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285
```